(12) United States Patent
Vadlamani et al.

(10) Patent No.: US 11,104,920 B2
(45) Date of Patent: *Aug. 31, 2021

(54) ENZYMATIC DIGESTION OF MICROALGAL BIOMASS FOR LIPID, SUGAR, AND PROTEIN RECOVERY

(71) Applicant: The University of Toledo, Toledo, OH (US)

(72) Inventors: Agasteswar Vadlamani, Toledo, OH (US); Patricia A. Relue, Toledo, OH (US); Sridhar Viamajala, Toledo, OH (US); Heng Shao, Toledo, OH (US); Sasidhar Varanasi, Toledo, OH (US)

(73) Assignee: The University of Toledo, Toledo, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/933,278

(22) Filed: Jul. 20, 2020

(65) Prior Publication Data

US 2020/0347414 A1    Nov. 5, 2020

Related U.S. Application Data

(63) Continuation of application No. 14/913,896, filed as application No. PCT/US2014/053421 on Aug. 29, 2014, now Pat. No. 10,752,924.

(60) Provisional application No. 61/871,997, filed on Aug. 30, 2013, provisional application No. 61/877,497, filed on Sep. 13, 2013.

(51) Int. Cl.
C12P 7/46 (2006.01)
C12P 19/02 (2006.01)
C12P 7/64 (2006.01)
C12P 19/14 (2006.01)
C12P 21/06 (2006.01)

(52) U.S. Cl.
CPC ............... *C12P 7/46* (2013.01); *C12P 7/6463* (2013.01); *C12P 19/02* (2013.01); *C12P 19/14* (2013.01); *C12P 21/06* (2013.01); *C12Y 302/01001* (2013.01); *C12Y 304/21014* (2013.01); *C12P 2203/00* (2013.01)

(58) Field of Classification Search
CPC .......... C12P 7/46; C12P 7/6463; C12P 19/14; C12P 21/06; C12P 19/02; C12P 2203/00; C12Y 302/01001; C12Y 304/21014
See application file for complete search history.

(56) References Cited

U.S. PATENT DOCUMENTS

| | | | |
|---|---|---|---|
| 2009/0203101 A1* | 8/2009 | Breneman | C12P 19/02 435/162 |
| 2011/0086386 A1* | 4/2011 | Czartoski | C12N 1/06 435/67 |

OTHER PUBLICATIONS

Choi et al. Enzymatic pretreatment of Chlamydomonas reinhardtii biomass for ethanol production. Bioresource Technology 101 (2010): 5330-5336.*

* cited by examiner

*Primary Examiner* — Iqbal H Chowdhury
(74) *Attorney, Agent, or Firm* — MacMillan, Sobanski & Todd, LLC

(57) ABSTRACT

Methods for the recovery of lipids, sugars, and proteins from microbial biomass by enzymatic digestion are disclosed. The methods involve treating microalgae with a fungal acid protease, or with a mixture of at least one protease and at least one amylase.

14 Claims, 15 Drawing Sheets
(4 of 15 Drawing Sheet(s) Filed in Color)

ENZYMATIC DIGESTION OF MICROALGAL BIOMASS FOR LIPID, SUGAR, AND PROTEIN RECOVERY

RELATED APPLICATIONS

This is a continuation application that claims priority to U.S. application Ser. No. 14/913,896, filed under 35 U.S.C. § 371 on Feb. 23, 2016, now allowed; which is the national phase entry of the international application PCT/US2014/053421, filed under the authority of the Patent Cooperation Treaty on Aug. 29, 2014, published; which claims priority to U.S. Provisional Application No. 61/871,997, filed under 35 U.S.C. § 111(b) on Aug. 30, 2013, and to U.S. Provisional Application No. 61/877,497, filed under 35 U.S.C. § 111(b) on Sep. 13, 2013. The entire disclosures of all the aforementioned applications are incorporated herein by reference for all purposes.

STATEMENT REGARDING FEDERALLY SPONSORED RESEARCH

This invention was made with government support under Grant number CHE1230609 awarded by National Science Foundation and Grant number DE-EE0005993 awarded by the United States Department of Energy. The government has certain rights in this invention.

BACKGROUND OF THE INVENTION

Rising petrochemical prices and interest in reducing $CO_2$ emissions have prompted the development of bio-based chemical production. As one example, succinate is an important platform chemical for the production of various high value-added derivatives such as 1,4-butanediol, ethylene diamine disuccinate, and adipic acid. Currently, succinate can be produced from either petrochemical synthesis or microbial fermentation, the latter process having a cost that could compete favorably with petrochemical production in the future. For bio-based succinic acid production, looking for the inexpensive feedstocks and optimization of the pretreatment process are important challenges in reducing the cost of the succinic acid production. Biological pretreatment methods, such as enzyme hydrolysis, have replaced the traditional acid hydrolysis due to the mild conditions, fewer by-products, and lack of corrosion issues. However, there remain many challenges and an unmet need in the art for more effective and cost-efficient methods of enzyme hydrolysis.

SUMMARY OF THE INVENTION

Provided herein is a method of enzymatic hydrolysis that comprises the steps of treating microalgae with enzymes to produce digested biomass, wherein the enzymes comprise a mixture of at least one protease and at least one amylase, and separating the digested biomass into an organic phase and an aqueous phase, wherein the organic phase contains lipids and the aqueous phase contains solids, carbohydrates, and peptides.

In certain embodiments, the method includes further processing and/or separating one or both of the organic phase and the aqueous phase to obtain lipids, solids, or bio-based products. In particular embodiments, the further processing and/or separating comprises subjecting the organic phase to a lipid-solvent separation to recover lipids. In particular embodiments, the further processing and/or separating comprises subjecting the aqueous phase to a solid-liquid separation to obtain separated solids and a supernatant, the supernatant containing carbohydrates and nutrients, and subjecting the supernatant to microbial fermentation to obtain a bio-based product. In certain embodiments, the bio-based product comprises succinic acid. In particular embodiments, the further processing and/or separating comprises subjecting the aqueous phase to microbial fermentation to obtain a bio-based product. In certain embodiments, the bio-based product comprises succinic acid.

In certain embodiments, the method further comprises extracting lipids from the solids with an organic solvent. In certain embodiments, the microalgae is lipid-rich wet microalgae.

Provided herein is a method of enzymatic hydrolysis comprising the steps of treating microalgae with one or more proteases to obtain digested biomass; separating the digested biomass into an organic phase and an aqueous phase, wherein the organic phase contains lipids and the aqueous phase contains solids, carbohydrates, and peptides; and treating at least a portion of the aqueous phase with one or more amylases to obtain an amylase-treated aqueous phase containing hydrolyzed carbohydrates and proteins.

In certain embodiments, the method comprises further separating and/or processing any of the organic phase, aqueous phase, or amylase-treated aqueous phase to obtain lipids, solids, or bio-based products. In particular embodiments, the further separating and/or processing comprises subjecting either the aqueous phase or the amylase-treated aqueous phase to microbial fermentation to obtain bio-based products. In particular embodiments, the further separating and/or processing comprises subjecting the aqueous phase or the amylase-treated aqueous phase to a solid-liquid separation to obtain solids and supernatant, and subjecting the supernatant to microbial fermentation to obtain bio-based products.

Further provided is a method of enzymatic hydrolysis comprising treating microalgae with an enzyme to product digested biomass, wherein the enzyme comprises a fungal acid protease, and separating the digested biomass into an organic phase and an aqueous phase, wherein the organic phase contains lipids and the aqueous phase contains solids, carbohydrates, and peptides. In certain embodiments, the method comprises further processing and/or separating one or both of the organic phase and the aqueous phase to obtain lipids, solids, or bio-based products. In particular embodiments, the further processing and/or separating comprises subjecting the organic phase to a lipid-solvent separation to recover lipids. In particular embodiments, the further processing and/or separating comprises subjecting the aqueous phase to a solid-liquid separation to obtain separated solids and a supernatant, the supernatant containing carbohydrates and nutrients; and subjecting the supernatant to microbial fermentation to obtain a bio-based product.

Further provided is a method of enzymatic hydrolysis comprising the steps of treating lipid-lean microalgae with a mixture of at least one protease and at least one amylase to obtain digested biomass; and further separating and/or processing the digested biomass to obtain a bio-based product. In certain embodiments, the further separating and/or processing comprises separating solids from liquid to obtain solids and a supernatant, the supernatant containing carbohydrates and nutrients; and subjecting the supernatant to microbial fermentation to obtain a bio-based product. In certain embodiments, the further processing comprises subjecting the digested biomass to microbial fermentation to obtain a bio-based product.

Further provided is a method of enzymatic hydrolysis involving a single step in which the release of lipids and breakdown of polysaccharides into simple fermentable sugars occurs simultaneously. The method utilizes an enzyme mixture comprising proteases, amylases, or a combination thereof. In certain embodiments, the method requires no pretreatment (thermal or mechanical) prior to enzymatic hydrolysis, and can be conducted at low temperatures using relatively simple equipment.

Further provided is a two-stage enzymatic hydrolysis method to extract lipids and hydrolyze sugars. In the first stage, a first set of enzymes is used to disrupt the cell wall, extract lipids, and at least partially hydrolyze the carbohydrates. In the second stage, a second set of enzymes is used to complete the hydrolysis of carbohydrates. In some embodiments, over 85% of lipids are extracted and 99% of the monomer sugars are released.

Further provided is a one-stage enzymatic hydrolysis method to extract lipids and hydrolyze carbohydrates simultaneously. The method involves using a mixture of enzymes comprising proteases, amylases, or a combination thereof.

Further provided is a method of fermentation, the method comprising using a mixture of enzymes to hydrolyze proteins in microalgae biomass and release nutrients into the hydrolysate, wherein the released nutrients and amino acids are used as a nitrogen source in fermentation without any further addition. In certain embodiments, solid residue is collected and optional steps can be performed to extract valuable products therein. In certain embodiments, the liquid phase of the microalgae hydrolysate is used in succinic acid fermentation without any further addition.

Further provided is a method of conducting succinic acid fermentation, the method comprising simultaneously disrupting the cell wall, releasing carbohydrates, and hydrolyzing the released carbohydrates into monomer sugars, all while using a mixture of enzymes from lipid-free microalgae. In certain embodiments, the method does not require any pretreatment prior to enzymatic hydrolysis and can be conducted at low temperatures using relatively simple equipment. This significantly reduces the cost of operation. In some embodiments, over 99% of the monomer sugar can be released under optimized conditions.

In certain embodiments, hydrothermal treatment is used to increase the accessibility of the enzymes to the binding sites on the polysaccharides, which significantly improves the enzyme activity and reduces the enzyme loading.

In certain embodiments, the mixture of enzymes hydrolyzes some of the protein content in the microalgae biomass and also releases other nutrients into the hydrolysate. The hydrolysate with released nutrients and amino acids (a nitrogen source) is used during the fermentation process of bio-based products without any further addition. The solid residue is collected and further steps can optionally be performed to extract valuable product in the solid residue. While using the liquid phase of microalgae hydrolysate in the succinic acid fermentation of certain embodiments, a similar yield (~72%, w/w) and activity is achieved between the fermentation with or without supplemental yeast extract.

Further provided is a method of enzyme hydrolysis comprising treating lipid-rich wet microalgae with proteases to produce digested biomass separable into an organic phase and an aqueous phase, wherein the organic phase comprises lipids and the aqueous phase comprises undigested solids and solubilized carbohydrates and peptides; and treating the aqueous phase with amylases to produce hydrolyzed carbohydrates and proteins. In certain embodiments, the method further comprises a separation step to separate the lipids from the organic phase. In certain embodiments, the aqueous phase is microbially fermented into bio-based products.

In certain embodiments, the method further comprises separating the undigested solids from the solubilized carbohydrates and peptides. In certain embodiments, the separated carbohydrates and peptides are microbially fermented into bio-based products.

In certain embodiments, the undigested solids are capable for use as animal feed or fertilizer. In certain embodiments, the hydrolyzed carbohydrates and proteins are fermented to produce bio-based products. In certain embodiments, the method further comprises separating solids from the hydrolyzed carbohydrates and proteins, wherein the separated solids are usable for animal feed or fertilizer.

Further provided is a method of enzymatic hydrolysis comprising treating lipid-rich wet microalgae with an enzyme cocktail comprising proteases and amylases to produce digested biomass; and separating the digested biomass into an organic phase and an aqueous phase, wherein the organic phase comprises lipids and the aqueous phase comprises undigested solids and solubilized carbohydrates and peptides. In certain embodiments, the method further comprises separating the organic phase into lipids and solvent, wherein the lipids are usable to produce fuels and other products.

In certain embodiments, the method further comprises microbially fermenting the aqueous phase to produce bio-based products. In certain embodiments, the method further comprises separating the aqueous phase into solids and a supernatant containing carbohydrates and nutrients, wherein the solids are usable for animal feed or fertilizer. In certain embodiments, the method further comprises microbially fermenting the supernatant to produce bio-based products.

Further provided is a method of enzymatic hydrolysis comprising treating lipid-lean wet algae with one of proteases or a combination of proteases and amylases, to produce digested biomass. In certain embodiments, the lipid-lean wet algae is thermally treated before being treated with enzymes. In certain embodiments, the method further comprises microbially fermenting the digested biomass to produce bio-based products. In certain embodiments, the method further comprises conducting a separation step on the digested biomass to produce solids and a supernatant, wherein the solids are usable for animal feed or fertilizer, and the supernatant comprises carbohydrates and nutrients. In certain embodiments, the method further comprises microbially fermenting the supernatant to produce bio-based products.

Further provided are the products of any of the methods described herein. In certain embodiments, the products comprise succinic acid.

BRIEF DESCRIPTION OF THE DRAWINGS

The patent or application file contains one or more drawings executed in color and/or one or more photographs. Copies of this patent or patent application publication with color drawing(s) and/or photograph(s) will be provided by the U.S. Patent and Trademark Office upon request and payment of the necessary fees.

DETAILED DESCRIPTION OF THE INVENTION

Figure 1:
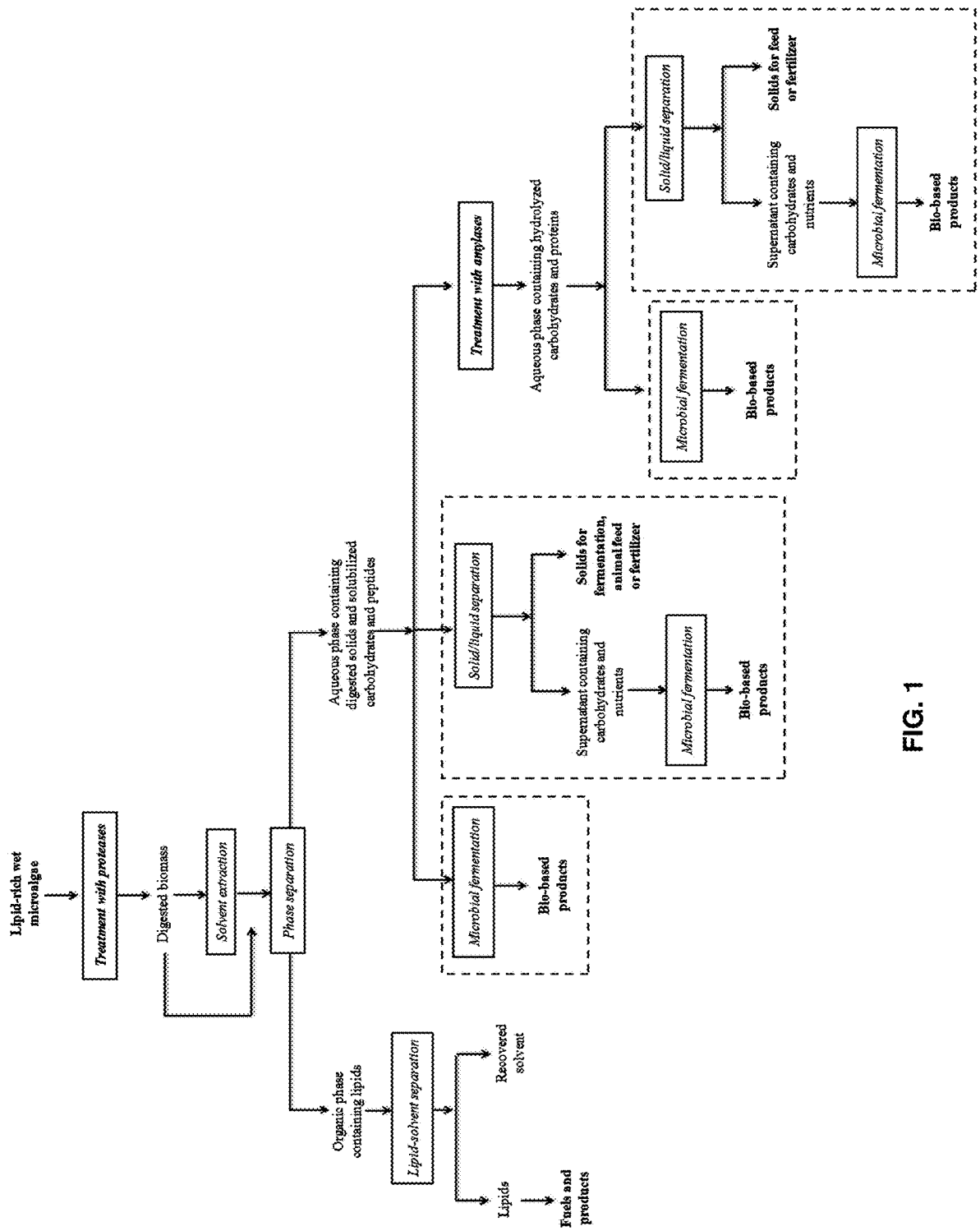
FIG. 1: Non-limiting example of a two-stage enzymatic hydrolysis of lipid-rich microalgae using proteases and amylases, in accordance with the present disclosure. The block flow diagram shows the process for production of sugar-rich hydrolysate and lipids from lipid-containing microalgae biomass with two stages of enzymatic hydrolysis. Recovered lipids may be used for production of fuels and other oleochemicals while the released sugars may be fermented (with or without solids separation) to bio-products such as alcohols, organic acids, or methane.

Throughout this disclosure, various publications, patents, and published patent specifications are referenced by an identifying citation. The disclosures of these publications, patents and published patent specifications are hereby incorporated by reference into the present disclosure in their entirety to more fully describe the state of the art to which this invention pertains.

Microalgae can serve as feedstocks for economically viable and environmentally sustainable biofuels due to their high productivity even while using low quality land, water, and nutrients. Unlike terrestrial plants, microalgae have a unicellular structure without lignin, which enables the breakdown of the cell wall and the release of carbohydrates with much milder pretreatment methods. As a result, microalgae do not generate significant amounts of inhibitors that cause degradation of carbohydrates during the process. Previously, microalgae have been subjected to mechanical disruption, thermolysis, microwave, and sonication methods to disrupt the cell wall. However, all of these methods require great energy consumption or higher equipment cost. The present disclosure describes the development of a cost-effective process with a low-energy requirement and easy setup of equipment that, in certain embodiments, simultaneously (1) disrupts the cell walls, (2) extracts the lipids, (3) releases and hydrolyses the polysaccharides to monomer sugars, and (4) releases and hydrolyses the proteins for a nitrogen source for fermentation.

Previously, marine algae were mainly used in the lipids production for biodiesel. Now, in accordance with the present disclosure, marine algae is converted to various kinds of bio-based chemicals like succinic acid. There are many advantages to using microalgae, as compared to terrestrial plants, as a feedstock for succinic acid production. These include no requirement for soil fertility and no need to draw upon valuable, and often scarce, supplies of freshwater. Moreover, the fixation and storage of $CO_2$ into the biomass while the microalgae grow reduces the concern of greenhouse gas release. Microalgae can be used as the biomass in lactic acid fermentation after the extraction of lipids. Algae biomass can also be used as a renewable energy feedstock like bio-ethanol or bio-hydrogen.

Microalgae biomass is conventionally formed by four principal biochemical classes of molecules: carbohydrates, proteins, nucleic acids, and lipids. For carbohydrates, different classes of microalgae produce particular types of polysaccharides. Usually, starch consisting mainly of amylose is the energy-storing carbohydrate found in most algae. For example, the green alga *Tetraselmis suecica* accumulates 11% and 47% of its dry weight as starch in nutrient replete and deplete conditions, respectively. Red algae synthesize a carbohydrate polymer known as floridean starch, consisting mostly of amylose. A commonly found polysaccharide in a large number of algal species is chrysolaminarin, a linear polymer of β-1,3 and β-1,6 linked glucose units. Different from lignocellulosic biomass, microalgae cells are single-cell organisms that are buoyant, evading the need for structural biopolymers such as hemicellulose and lignin which, otherwise, are important for supporting tissue in land plants.

Besides carbohydrates, microalgae also contain proteins that are important enzymes in the regulation of cell metabolism or cross-linked hydroxyl-proline-rich glycoproteins as the structural cell wall. As with carbohydrates, lipids serve both as energy reserves and structural components (membranes) of the cell. The simple fatty acid triglycerides are important energy reserves. Membranes are mainly constructed from phospholipids and glycolipids, where the hydrophilic polar phosphate or sugar moieties and the level of saturation of the fatty acyl chains determine the fluidity of the membranes. For some microorganisms, starch-rich cultures may be directly usable as feedstock in fermentation, although pretreatment and/or enzymatic digestion could be advisable to improve the productivity. Additionally, carbohydrate-rich microalgae residues remaining after lipid extraction can be feedstock for succinic acid production.

Some strains of microalgae accumulate lipids, such as triglycerides, which can be converted to biodiesel, green diesel, or high-value oleochemicals. In addition to cost- and energy-efficient methods for the recovery of lipids, a conversion process developed for microalgae should be able to preserve the other major components—carbohydrates and protein—for profitable uses. Such conversion processes should also be able to directly utilize wet biomass because drying processes are energy-intense. In certain embodiments, the methods described herein advantageously preserve carbohydrates and proteins, and are capable of utilizing wet biomass. To recover triglycerides and other lipids from wet material, cell disruption is important. Mechanical disruption is commonly applied either in the form of intense shear stresses, ultrasonic waves, or electromagnetic fields. Since these forces are most effective over short ranges, the slurries are passed through narrow and restricted zones where intense forces are applied to disrupt the robust microalgal cell walls. As a result, processes based on mechanical disruption can be energy- and capital-intense as well as difficult to scale up.

Others have previously attempted to use enzymes for digestion of algal cells with the intent to recover lipids and/or carbohydrates. For example, cocktails of thermostable enzymes containing up to 14 different enzymes including several endo- and exo-gluconases have been attempted. While these cocktails produced some lipid recovery, protease activity was absent in the cocktails and amylase was present only in minor quantities. One cocktail that contained higher amounts of amylase was relatively ineffective in facilitating lipid release. Nonetheless, lipid release was measured by gravimetric methods which usually overestimate lipid content, and the enzymes used in these attempts were not commercially available.

Enzymes have been previously used to degrade cell walls, but have not been previously shown to enable either recovery of lipids or breakdown of carbohydrates to monomeric sugars. Previous attempts have shown that amylases did not have any impact on cell wall degradation, resulting in a belief that lysing enzymes from *Aspergillus* sp. was ineffective towards algal cells. In stark contrast to the previous attempts by others, the present disclosure reveals that protease alone is effective in digesting algal biomass and releasing lipids that phase-separate or can be recovered using solvent extraction methods. The lipids can be recovered through solvent extraction with non-polar organic solvents, a mixture of polar and non-polar organic solvents, or switchable polarity solvents, and the lipids can be subsequently converted to fuels or oleochemicals. The protease-alone treatment also partially hydrolyzes algal polysaccharides to monomeric sugars. Supplementation of the protease with α-amylase and glucoamylase allows for near-complete hydrolysis of carbohydrates to sugars, in addition to simultaneously releasing lipids. The synergistic action of protease and amylase together drastically reduces the amount of amylase required for hydrolysis of algal carbohydrates. Furthermore, after removal of lipids, the sugar-rich aqueous phase is easily fermentable by microorganisms, and the residual protein and other cellular material can serve as the nutrient (nitrogen, phosphorus, and other micronutrients) source to support microbial growth. As a result, several process options are described, the several processes varying by the biochemical composition of the algal biomass.

Provided herein are methods of enzymatic hydrolysis that involve a single-step in which the release of lipids and breakdown of polysaccharides into simple fermentable sugars occur simultaneously. The methods provide for a cost-effective process for the recovery of lipids, sugars, and proteins from microbial biomass by enzymatic digestions. These methods remove the costs associated with drying algae and a separate extraction of lipids, resulting in a significant cost advantage over methods known in the art. By contrast, in multi-step processes, lipid extraction from dry algae is carried out before the remaining residue is subjected to enzymatic hydrolysis or acid digestion, producing an economically disadvantageous result. The methods of the present disclosure utilize a specific enzyme cocktail comprising proteases, amylases, or a combination thereof, as opposed to enzymes from lignocellulases. This further reduces the costs involved. In certain embodiments, the depolymerization of all the major algal biopolymers occurs in a single step through the use of a low-cost and abundant enzyme cocktail containing a mixture of proteases and amylases.

The methods described herein do not involve any acid digestion step. This provides an advantage over other methods which use acid digestion to hydrolyze the carbohydrates. Acid digestion typically produces inhibitors from sugar degradation that inhibit the fermentation process, thereby hindering the conversion of sugars to value-added products. The methods herein also do not require the presence of free cysteine, a sulfur-containing amino acid, in order to activate the enzymes. The enzymes used herein are active without having to add exogenous cysteine to the digestion medium. Without wishing to be bound by theory, it is believed this is due to the action of the particular proteases used. In one non-limiting example, the proteases digest the microalgae while simultaneously hydrolyzing at least 10% of protein and carbohydrates.

An alternative method to release lipids under milder operating conditions than mechanical methods is through the use of enzymes to digest cells. However, the overall economic viability of enzyme-based processes depends on the cost and ease of enzyme production. Commercially available, low-cost enzymes are thus most desirable. Some commercial α-amylase exhibits the ability to degrade the glycoproteins within cell walls. In addition, alpha-amylase can liquefy the intracellular starch to dextrins, which can be further saccharified to the sugar monomers by glucoamylase. The enzymatic pretreatment of microalgae biomass for ethanol production by *S. cerevisiae* S288C needs two steps of the enzymatic hydrolysis: liquefaction by thermostable α-amylase in 90° C. first at pH 6.0, then saccharification in 55° C. at pH 4.5. The protease from fungi can hydrolyze the glycoprotein, the major structure in the microalgae cell wall, and there is also some α-amylase and glucoamylase blended in the protease since they are the by-products of the protease in the production by those fungi. In accordance with the present disclosure, these mixed enzymes can work together to break the cell wall and the carbohydrates at the same time. This process can be performed in low temperatures from 30° C. to 50° C., and pH from 3 to 5. Moreover, most of the sugar is released in less than 1 hour. Since the protease loses the activity quickly (mostly in less than 2 hours), it does not bother the microorganism's growth in the further fermentation.

Beside the carbon source, nitrogen is an indispensable nutrient for the growth and metabolism of microorganism cells. Any kind of nitrogen source feeding (ammonium, free amino acid, urea, or yeast extract) can increase the fermentation rate and improve the growth of cells. A lack of nitrogen nutrition will lead to the reduction of succinic acid formation rate and yield, and such negative effect cannot be ignored particularly when the succinic acid concentration in the medium is required at higher levels. In industrial processes, an additional nitrogen source feeding is necessary and costs a considerable part of the total succinic acid cost. Some microalgae biomass contains a considerably high level of protein (over 20% in dry weight), which can be derived to the free amino acid during the pretreatment process by protease. Therefore, the nitrogen-rich microalgae can serve as the alternative low-cost nitrogen source in the succinic acid fermentation.

In non-limiting examples, *Actinobacillus succinogenes* is described as the microorganism in the fermentation, which is flexible in its ability to efficiently ferment different carbon sources commonly found in hydrolysate, including L-arabinose, cellobiose, fructose, galactose, glucose, lactose, maltose, mannitol, xylose, and others. The metabolic pathways for both hexose and pentose sugars show that these sugars may be completely converted to mostly succinate, with acetate, formate, and alcohol as the main by-products. It is to be understood, however, that the use of microorganisms other than *Actinobacillus succinogenes* is possible. Suitable other microorganisms include, but are not limited to: microorganisms of the genus *Lactobacillus*; microorganisms of the genus *Pseudomonas*; microorganisms of the genus *Bacillus*; or microorganisms of the genus Clostridia, such as *Clostridium autoethanogenum, Clostridium ljundahlii,* or *Clostridium ragsdalei.*

Unlike the terrestrial lignocellulosic biomass, most microalgae are single-celled and do not contain lignin. Some algae species even lack cell walls. This structure allows for much milder conditions and a simpler pretreatment process, which reduces the cost caused by higher temperatures and corrosion in the energy-intensive process. First, the microalgae cell wall is disrupted by the acid protease, a low cost enzyme produced from fungi. In addition, most of their reserved carbohydrates in the cell are starch-like polysaccharides, which can be hydrolyzed by low-cost enzymes such as α-amylase and amyloglucosidase to sugar monomers like glucose, galactose, xylose, or mannose. All of these released sugars can be directly utilized by most of the strain such as the yeast to produce ethanol, or *Actinobacillus succinogenes* to produce succinic acid.

In one aspect, described herein is a method in which an optimized enzymatic hydrolysis process is used to substitute the conventional energy-intensive pretreatment for microalgae biomass. For microalgae, the main obstacle of enzymatic hydrolysis is that intercellular starch granules are bound within rigid cell walls, requiring a biomass pretreatment step to break down the cell wall and release polysaccharides such as starch, structural carbohydrates, and other nutrients, prior to enzymatic hydrolysis and fermentation steps. The cell wall of microalgae contains glycoproteins as the predominant constituents in its extracellular matrix. Therefore, degrading those proteins is an important step to disrupt the whole cell wall. Some exhibit the protease activity particular to the degradation of glycoproteins within cell walls. However, using α-amylase only to break the cell wall is not quite efficient enough to recover a high sugar yield. To solve this problem, one embodiment of the present disclosure replaces α-amylase with protease from the same fungi strain (*Aspergillus oryzae*), which actually also contains a small amount of α-amylase and glucoamylase. This enzyme mixture allows for the full disruption of the cell wall to occur simultaneously to the hydrolysis of the polysaccharides to monomer sugars. While the microalgae grow to a certain concentration, the microalgae biomass can be collected and concentrated by settling or centrifugation. In certain embodiments, the pH of the slurry can then be adjusted to about 4.5 by adding citrate salt buffer (50 mM). Then, α-amylase (EC 3.2.1.1) and protease (EC 232.752.2) from *Aspergillus oryzae* and amyloglucosidase (EC 3.2.1.3) from *Aspergillus niger* are added into the broth to initiate the hydrolysis process. These two enzymes can be added simultaneously because they share a similar range of optimized temperature (30-55° C.) and pH (3.0-5.5).

Using the hydrothermal pretreatment reduces the enzyme loading by increasing the accessibility of the enzymes to the binding sites on polysaccharides, which in turn makes the whole process more cost-effective. Similar to the lignocellulosic biomass, applying the hydrothermal pretreatment recrystallizes the cellulose so that the hydrolytic enzymes can easily access the biopolymers. The autoclave equipment can be applied to the hydrothermal pretreatment up to 120° C., which is high enough to partially breakdown the cell wall and extracellular matrix of the microalgae. After this treatment, the enzyme has a greater chance to bind the reaction sites on the intracellular polysaccharides due to the cell wall break. As a result, fewer enzymes are required to reach the same activity. By way of a non-limiting example, autoclaving at 120° C. for 30 minutes can reduce over 60% of the α-amylase loading to achieve the same sugar yield.

In addition, the protein content and other nutrients in the microalgae are released and soluble after the enzymatic hydrolysis, which can be used as the nitrogen and phosphate source in a fermentation process. The solid residue of microalgae biomass after the enzyme hydrolysis can be removed by centrifugation and used to produce value-added products in further steps.

Referring now to FIG. 1, provided herein is a method for a two-stage enzymatic hydrolysis of lipid-rich microalgae using proteases and amylases. The block flow diagram in FIG. 1 shows a two-stage process where protease is used alone in the first stage for cell disruption and the recovery of lipids. After treatment with extraction solvents, the aqueous phase is treated with additional amylases, if necessary, to break down additional polysaccharides to monomeric sugars. Treatment with amylases hydrolyzes carbohydrates into monomeric or oligomeric saccharides. The lipids are recovered from the organic phase through evaporation. The aqueous phase can be filtered to recover protein-rich residues while leaving behind the soluble sugars, protein, and other cellular material for fermentation into products such as, but not limited to, alcohols, organic acids, or methane. Alternatively, the whole slurry can be fermented.

Figure 2:
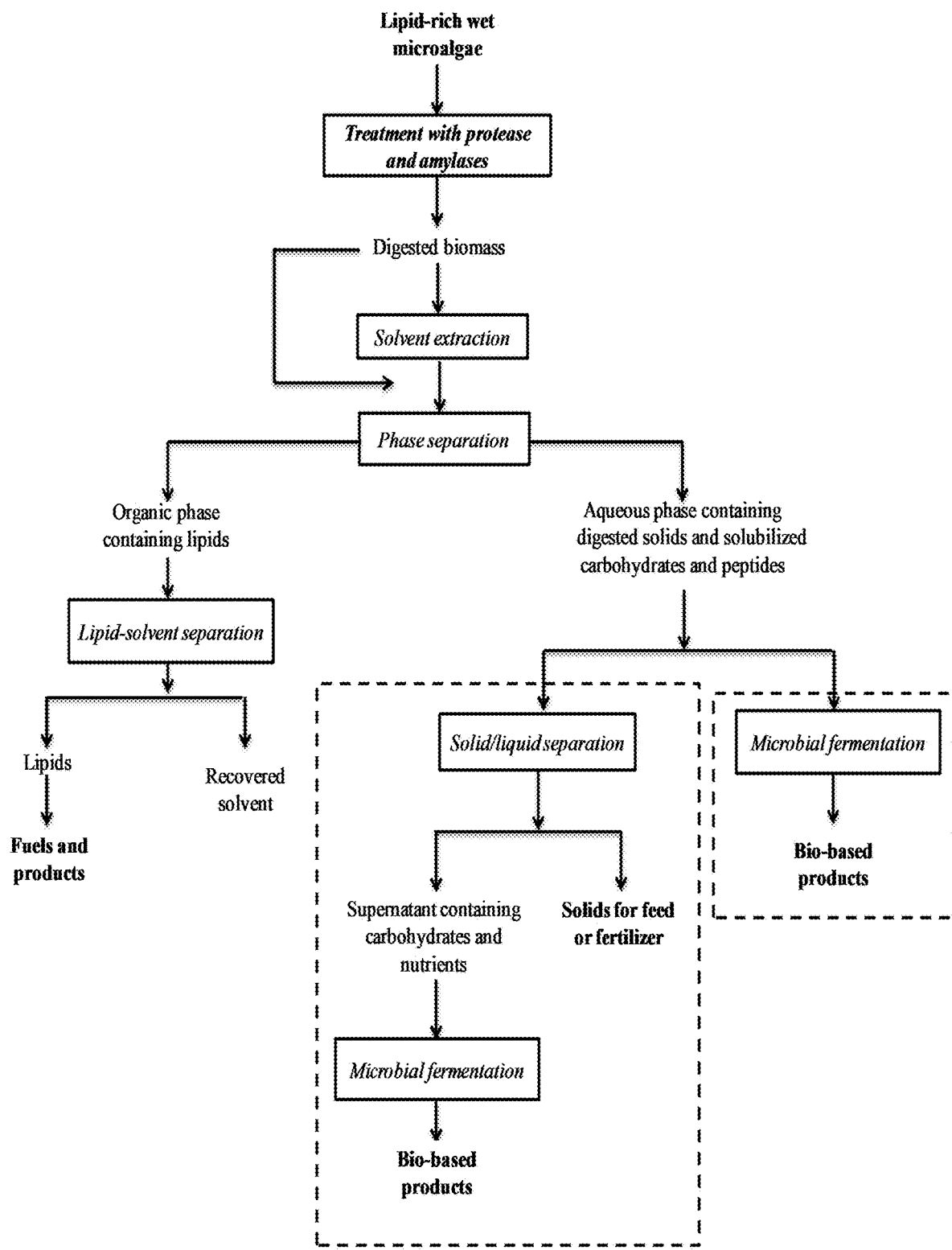
FIG. 2: Non-limiting example of a one-stage enzymatic hydrolysis of lipid-rich microalgae using a mixture of proteases and amylases. The block flow diagram shows the process for the production of sugar-rich hydrolysate and lipids from lipid-containing microalgae biomass with one stage enzymatic hydrolysis. Recovered lipids may be used for production of fuels and other oleochemicals while the released sugars may be fermented (with or without solids separation) to bio-products such as alcohols, organic acids, or methane.

Referring now to FIG. 2, provided herein is a method for a one-stage enzymatic hydrolysis of lipid-rich microalgae using a mixture of proteases and amylases. The block flow diagram in FIG. 2 shows a one-stage process that incorporates simultaneous treatment with a mixture of protease and amylase, and produces sugar-rich hydrolyzate and lipids. In this process, cell digestion and polysaccharide hydrolysis are completed in a single step. Subsequent recovery and conversion pathways are similar to those shown for the two-stage process. The recovered lipids are capable of use in the production of fuels and other oleochemicals, while the sugars can be fermented into bio-products such as, but not limited to, alcohols, organic acids, or methane.

Figure 3:
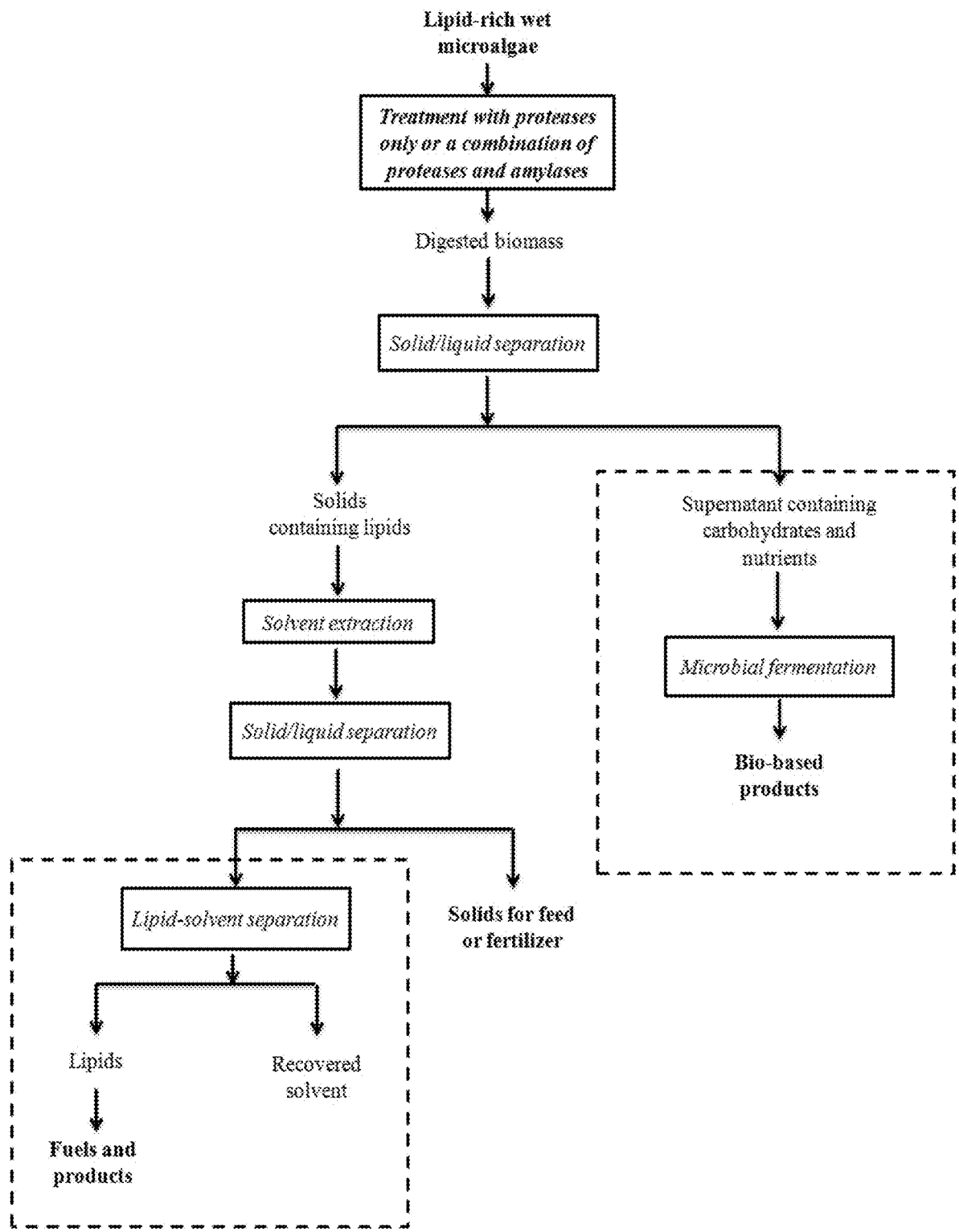
FIG. 3: Non-limiting example of enzymatic hydrolysis of lipid-rich microalgae using either a mixture of protease and amylases or protease alone. Following enzyme treatment, the hydrolyzate is first separated into residual solids and supernatant. The residual solids undergo solvent extraction to recover lipids while the supernatant containing hydrolyzed sugars and protein is fermented into bio-products such as alcohols, organic acids, or methane.

Referring now to FIG. 3, provided herein is an alternate method of enzymatic hydrolysis of lipid-rich microalgae using either a mixture of protease and amylases or protease alone. Following the enzyme treatment, the hydrolyzate is first separated into residual solids and supernatant. The residual solids undergo solvent extraction to recover lipids while the supernatant containing hydrolyzed sugars and protein is fermented into bio-products such as, but not limited to, alcohols, organic acids, or methane.

Figure 4:
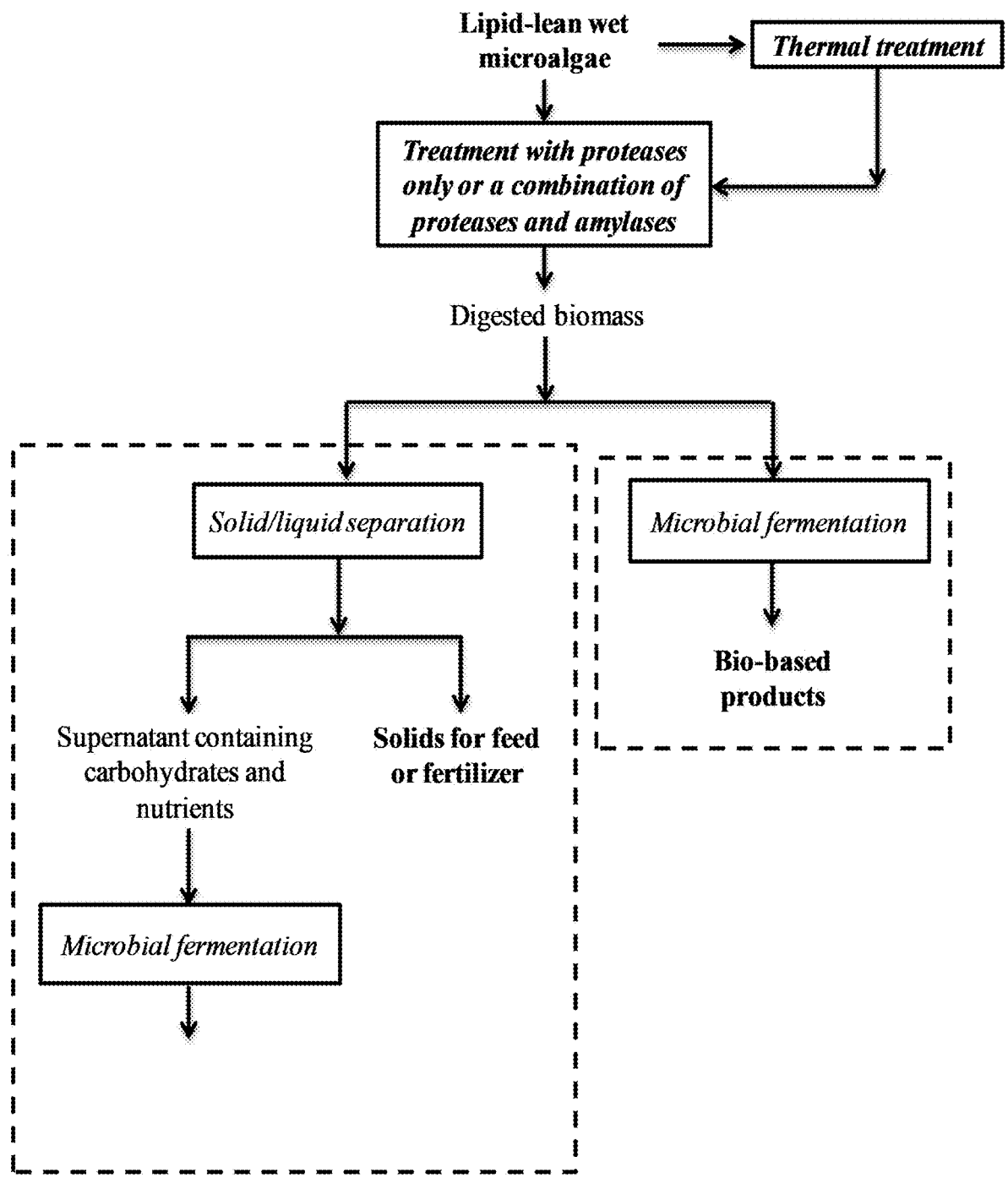
FIG. 4: Non-limiting example of enzymatic hydrolysis of lipid-lean microalgae using protease alone or in combination with amylases. Following enzyme treatment, the hydrolysate may be fermented (with or without prior separation of insoluble solids) to bio-products such as alcohols, organic acids, or methane.

Referring now to FIG. 4, provided herein is a method of enzymatic hydrolysis of lipid-lean microalgae. These microalgae are rich in carbohydrates but do not contain significant amounts of lipids. For such microalgae, using proteases alone or in combination with amylases accomplishes the release of cellular polysaccharides as monomeric sugars. Following the enzyme treatment, the hydrolyzate can be fermented, with or without prior separation of insoluble solids, into bio-products such as, but not limited to, alcohols, organic acids, or methane. FIG. 4 shows a block flow diagram for this one-stage process. Thermal treatments can also be used to reduce enzyme loading.

It is to be understood that any suitable solvent extraction can be performed to achieve separations. A solvent extraction is a method for separating a substance from one or more other substances by using a solvent, the method relying on variations in the solubilities of different compounds in the different substances. The substance to be extracted is typically dissolved in a liquid, and a liquid solvent is used for the extraction. A solvent is chosen that does not mix with the compound in which the substance of interest is dissolved, such that when left undisturbed, two separate layers will form. Once the solvent is added, the two liquids may be shaken together for a time and then allowed to stand for a time until they separate out. The skilled practitioner will recognize that the choice of solvent will depend on the chemical and physical properties of all the substances in the mixture. In certain methods, the solvent extraction is carried out in several stages using different solvents. In one non-limiting example, the solvent is a mixture of hexane and iso-propanol, but many other polar or non-polar solvents, or mixtures of polar or non-polar solvents, can be used. Other possible extraction solvents include, but are not limited to: chloroform, methanol, heptane, hexane, iso-propanol, and mixtures thereof. In some non-limiting examples, a 2:1 (v/v) mixture of chloroform and methanol is used. In other non-limiting examples, a mixture of hexane and iso-propanol is used.

In certain embodiments, the methods described herein are able to simultaneously accomplish lipid release and carbohydrate breakdown into simple sugars, in addition to the partial hydrolysis of algal protein.

Though *Chlorella* species and *Schizochitrium limacium* are described for exemplary purposes, it is to be understood that the methods described herein can be performed with any suitable microalgae. There are more than 50,000 known species of microalgae. Suitable species of microalgae include, but are by no means limited to: species of the *Chlorella* genus; species of *Spirulina* genus; *Schizochitrium limacium*; *Botryococcus braunii*; species of the genus *Isochrysis*, such as *Isochrysis galbana*; *Neochloris oleoabundans*; *Phaeodactylum tricornutum*; *Pleurochrysis carterae*; *Prymnesium parvum*; *Scenedesmus dimorphus*; *Tetraselmis chui*; and *Tetraselmis suecica*. In general, any green algae species can be used in the methods described herein.

The enzymatic treatment described herein allows for the simultaneous release of lipids and breakdown of polysaccharides into simple sugars. In some embodiments, at least 5% of non-polar lipids spontaneously separate from the aqueous phase, allowing for recovery of lipids without the need for an extraction step. In one non-limiting example, at least 85% of lipids are extracted and at least 99% of monomer sugars are released. In another non-limiting example, at least 20% of protein and carbohydrates are hydrolyzed. In another non-limiting example, cellular lipids are released while at least 20% of other cellular components are simultaneously hydrolyzed.

The methods are cost-effective for many reasons, such as being able to be conducted at low temperatures. The methods are conducted below the temperature of gelatinization of the substrate. In one non-limiting example, the temperature is about 50° C. and the pH is about 4.5. In one non-limiting example of a method with a hydrothermal treatment, an autoclave is used at 120° C. for 30 minutes, and the pretreatment results in reducing enzyme loading to ⅓ while still reaching the same yield of sugar. In one non-limiting example, over 99% of the monomer sugars are recovered in less than 2 hours, and over 99% of the lipids are released.

The aqueous phase from any of the methods can be used as a nitrogen source in a fermentation process to produce products such as, but not limited to, alcohols, organic acids (like succinic acid), or methane. In some embodiments, the microalgae residue following enzymatic hydrolysis is used as a nitrogen and phosphate source in succinic acid fermentation without an external nutrient. The separated solids recovered from the methods are useful for microbial fermentation, or as animal feed or fertilizer. In some embodiments, lipids become stuck on the solids after enzymatic digestion. When this occurs, the digested solids can be treated with an organic solvent to recover the lipids.

EXAMPLES

Example 1—Recovery of Lipids and Monomeric Sugars from Wet Algal Biomass Using Enzymatic Treatment Methods Two strains of algae were used in these experiments: a) *Chlorella* sp. SLA-04, and b) *Schizochitrium limacium* SR21, obtained from ATCC (MYA 1381).

Biomass digestions were performed at a solid concentration of 10% (w/v) in 50 mM citrate buffer adjusted to a pH of 4.5. Protease alone or a mixture of protease with α-amylase and amyloglucosidase (all purchased from Sigma) were added to the biomass slurries. Enzyme loadings (per g-biomass) used were as follows—(a) protease 312 U/g; (b) α-amylase 1875 U/g; and (c) glucoamylase 18.75 U/g. 1 α-amylase unit is defined as the amount of enzyme that liberates 1 μmol maltose per minute at pH 6.0 and 25° C.; 1 glucoamylase unit is defined as the amount of enzyme which cleaves 1 μmol of maltose per min at pH 4.3 and 25° C.; and 1 protease unit is defined as the amount of enzyme which hydrolyzes 1 μmol of L-leucine-p-nitroanilide per min.

The algae-enzyme mixture was incubated at 50° C. for 6 h in a shaker maintained at 200 rpm. Biomass-free control experiments were also performed. Samples were taken at regular intervals during the experiments to measure released lipids and sugars.

For lipid recovery and analysis, a 3:2 (v/v) mixture of hexane/iso-propanol was used. 0.5 mL of the solvent mixture was added to 300 μL of the digested samples and extraction was carried out at 90° C. for 30 min. Lipids in the extraction solvent were analyzed and quantified using a gas chromatograph (GC) connected with a flame ionization detector (FID). For soluble carbohydrate analysis, the digested samples were centrifuged and filtered through a 0.22 μm membrane and the supernatant was analyzed for sugars via HPLC using a Shodex SH1011 ion exchange column with refractive index (RI) detector.

In another set of experiments, after enzymatic digestion of SLA-04, the digested slurry was centrifuged and the residual solids were extracted with hexane/iso-propanol.

Figure 5A:
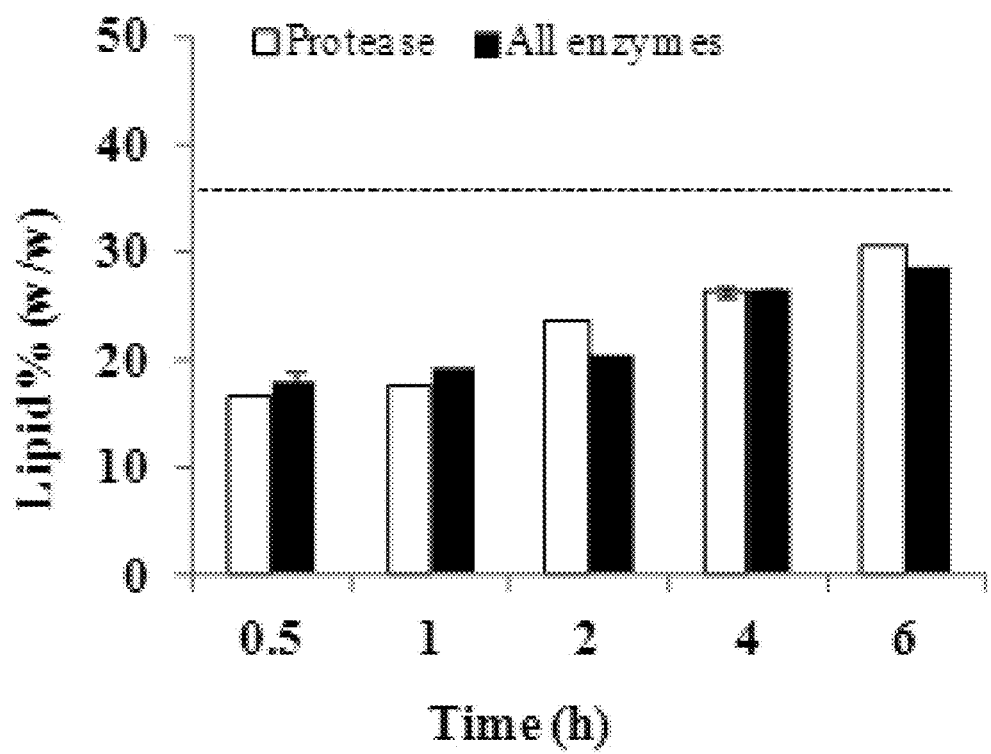
FIGS. 5A-5B: A fraction of lipid extractable after enzymatic treatment of SLA-04 (FIG. 5A) and SR-21 (FIG. 5B) after enzymatic digestion with protease (open bars) or a mixture of protease and amylases (filled bars). The horizontal dashed line indicates the total fatty acid methyl ester (FAME) content of the biomass samples—35% (w/w) for SLA-04 and 44% (w/w) for SR21.
Figure 5B:
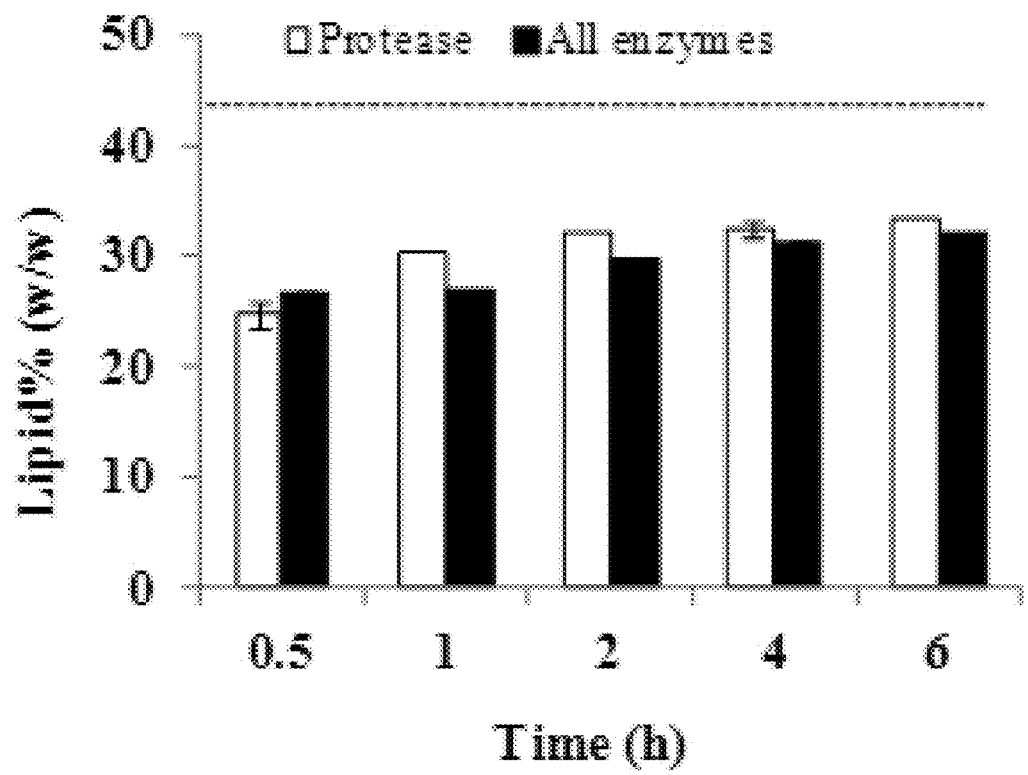

From FIGS. 5A-5B, it can be seen that the rate and extent of lipid released from both algae material (SLA-04 and SR-21) is similar in treatments with protease alone as well as in treatments with a mixture of protease and amylases. For SLA-04, >85% of the lipid (measured as fatty acid methyl ester—FAME) contained in the biomass was released (and extracted) as a result of the enzymatic treatments. For SR-21, >72% of the cellular lipid was released. Enzyme-free control treatments did not release any extractable lipids.

Figure 6:
FIG. 6: Photograph showing lipid droplets formed on the surface of the water phase in enzymatically digested SLA-04.
Figure 7A:
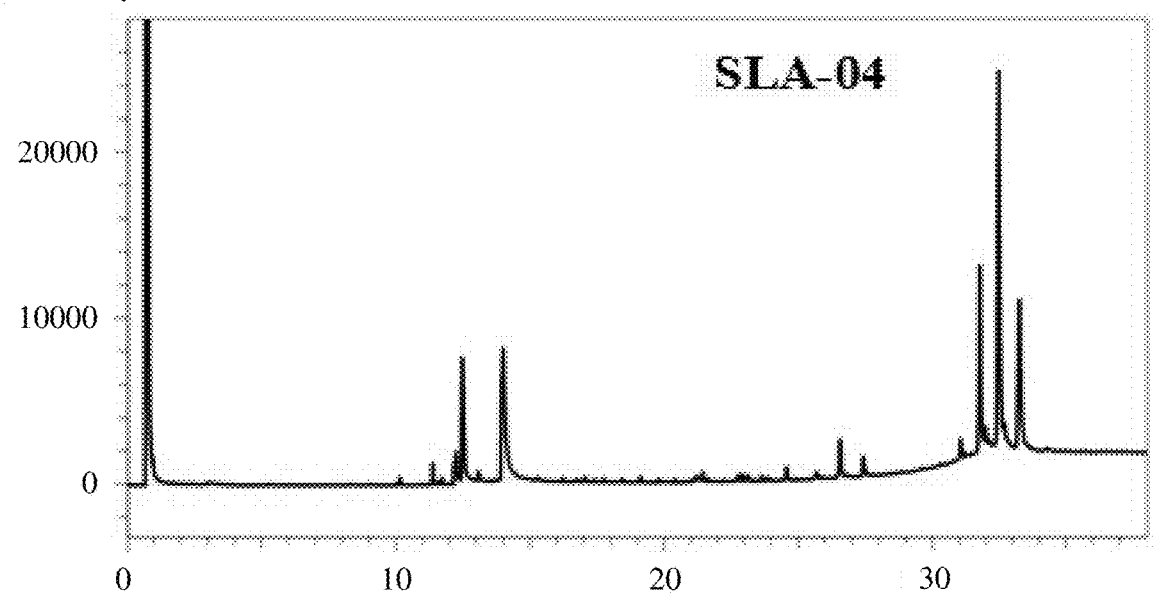
FIGS. 7A-7B: A non-limiting example GC chromatogram of solvent extracts obtained after digestion and recovery of lipids from SLA-04 (FIG. 7A) and SR-21 (FIG. 7B). This shows that most of the recovered lipids were triglycerides (retention time>30 min).
Figure 7B:
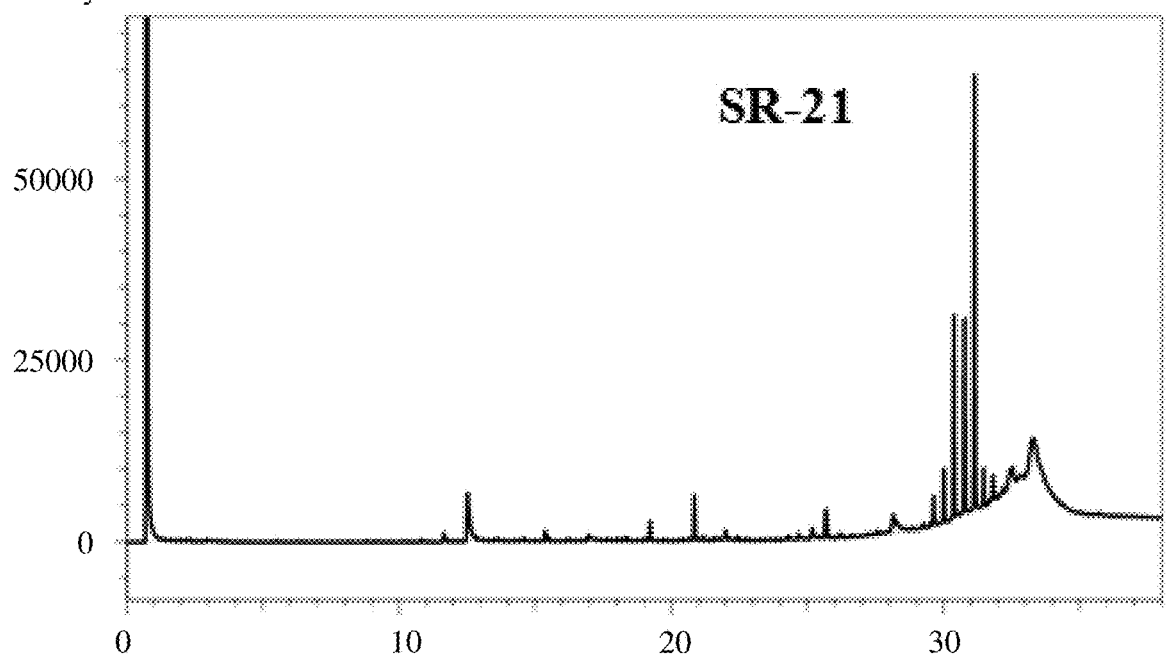
Figure 8:
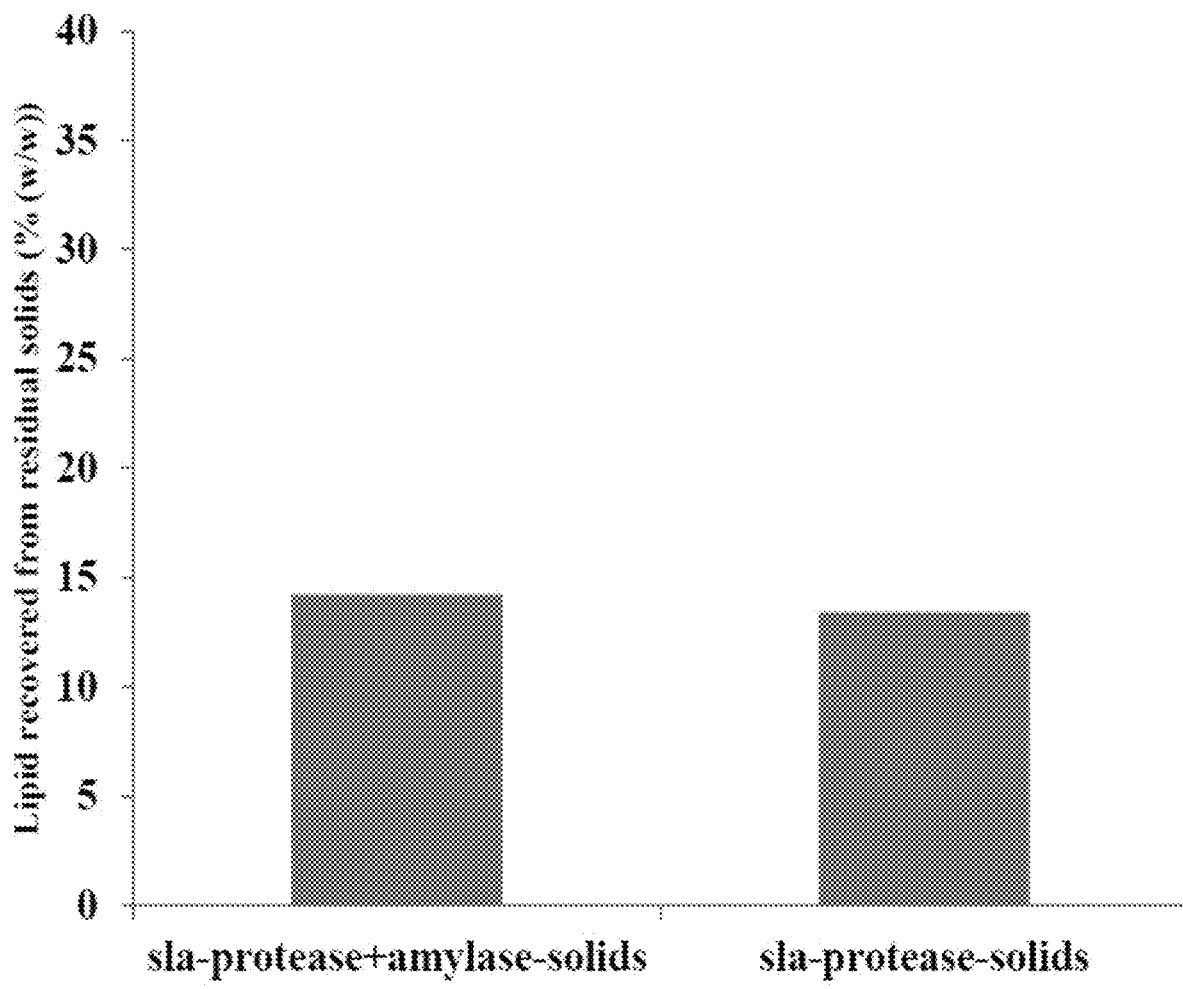
FIG. 8: Graph showing that a portion of lipids can remain stuck to residual solids following enzymatic digestion, and can be extracted separately. The y-axis shows the mass of lipids recovered from residual solids relative to the initial mass (feed) of algae biomass.

FIG. 6 shows that at least a portion of the lipids released during digestion separated into an oil phase and could be separated without the need for solvent extraction. FIGS. 7A-7B show that most of the lipids recovered after extraction were triglycerides. FIG. 8 shows that at least a portion of the lipids remained associated with the residual solids and could be extracted separately. The y-axis in FIG. 8 shows the mass of lipids recovered from residual solids relative to the initial mass (feed) of algae biomass.

Figure 9A:
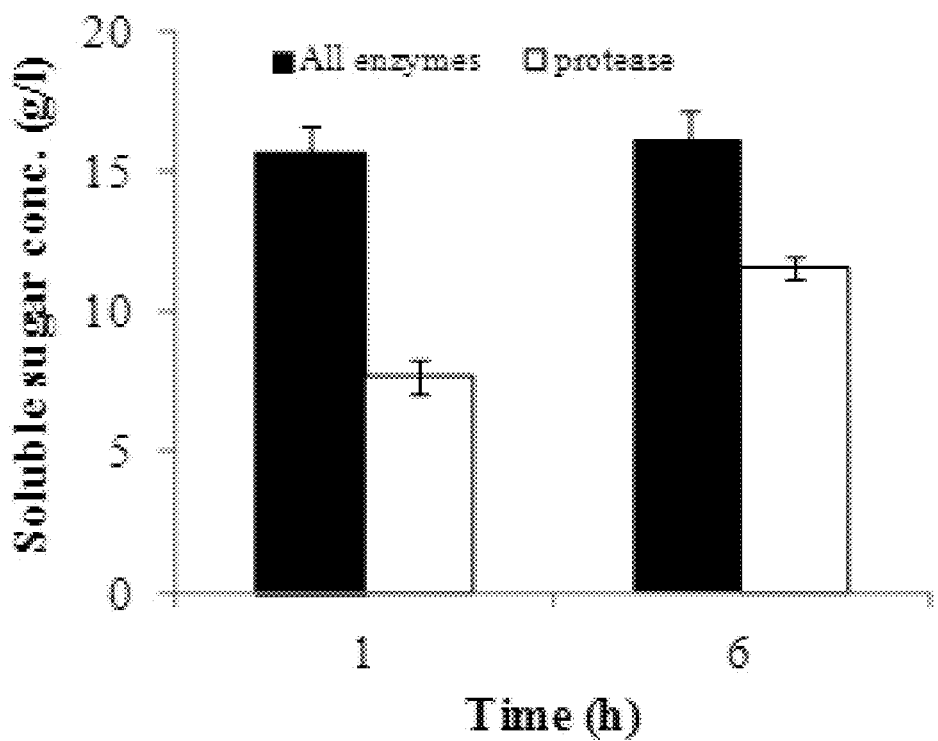
FIGS. 9A-9B: Concentrations of solubilized sugars released from SLA-04 (FIG. 9A) and SR-21 (FIG. 9B) after enzymatic digestion with protease (open bars) or a mixture of protease and amylases (filled bars).
Figure 9B:
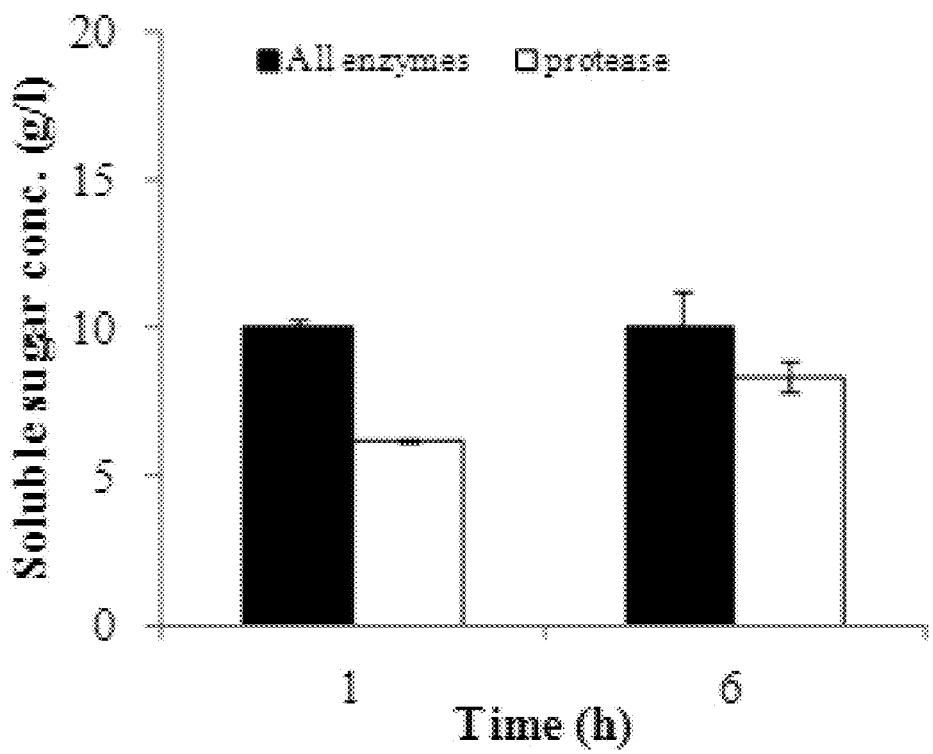

After enzyme treatment, solubilized monomeric sugar concentrations were measured in the digested slurries to determine if carbohydrate hydrolysis also occurred during the treatments. FIGS. 9A-9B show that treatments with protease alone as well as treatments with a mixture of protease and amylases resulted in release of monomeric sugars from both algal biomass samples (SLA-04 and SR-21). However, the extent of sugar release was greater in the treatments that contained amylases. Glucose was the major sugar recovered along with smaller amounts of xylose. Gel electrophoresis of the three enzyme preparations (FIG. 10) shows that there may be some amylase activity present in the commercial protease preparation that may have resulted in some hydrolysis of carbohydrates even in the absence of the amylases.

Example 2—Sugar Recovery from Microalgal Biomass by Enzymatic Digestion

Enzymatic hydrolysis experiments were conducted using protease, α-amylase, and glucoamylase, and their combinations. A mixed culture of lipid-lean algal biomass (lipid content<5% (w/w)) was obtained from a commercial wastewater treatment facility. The biomass had a carbohydrate content of 24.5% (w/w). The digestion experiments were performed at a solids' loading of 16% (w/v) at a pH of 4.5. The amount of each enzyme was fixed as follows: 2.5 kU protease, 5 kU of α-amylase, and 150 U of glucoamylase. Enzymatic hydrolysis reactions were performed in sealed serum vials agitated at 200 rpm for 2 h at 55° C. Samples were collected at the end of the incubation period and analyzed by HPLC using a Shodex SH1011 ion exchange column with refractive index (RI) detector.

Figure 10:
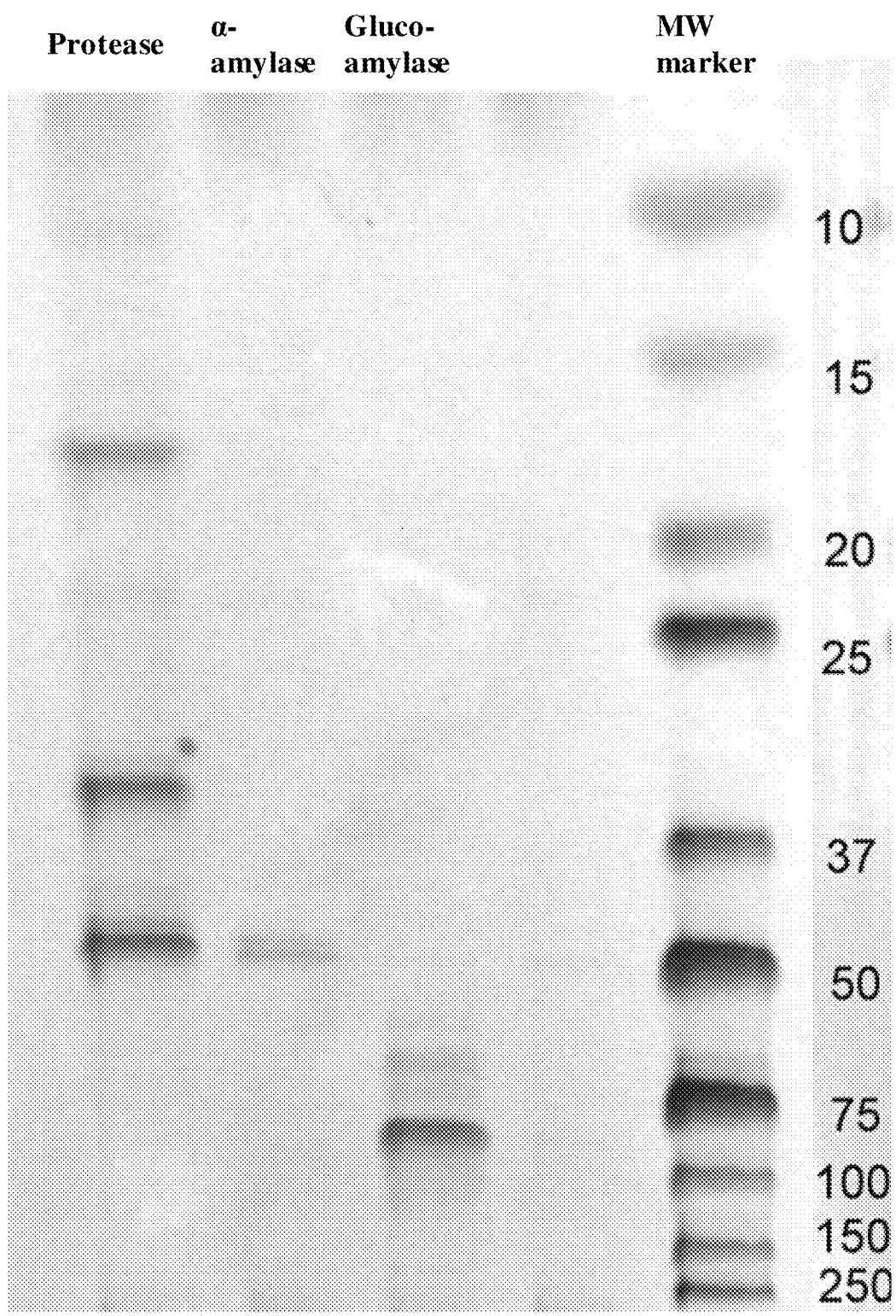
FIG. 10: Image of a PAGE electrophoresis gel for commercial protease, α-amylase, and glucoamylase enzyme preparations. The image shows that some α-amylase activity might be present in the protase preparation (see overlapping band at ~50 kD in lanes 1 and 2).
Figure 11:
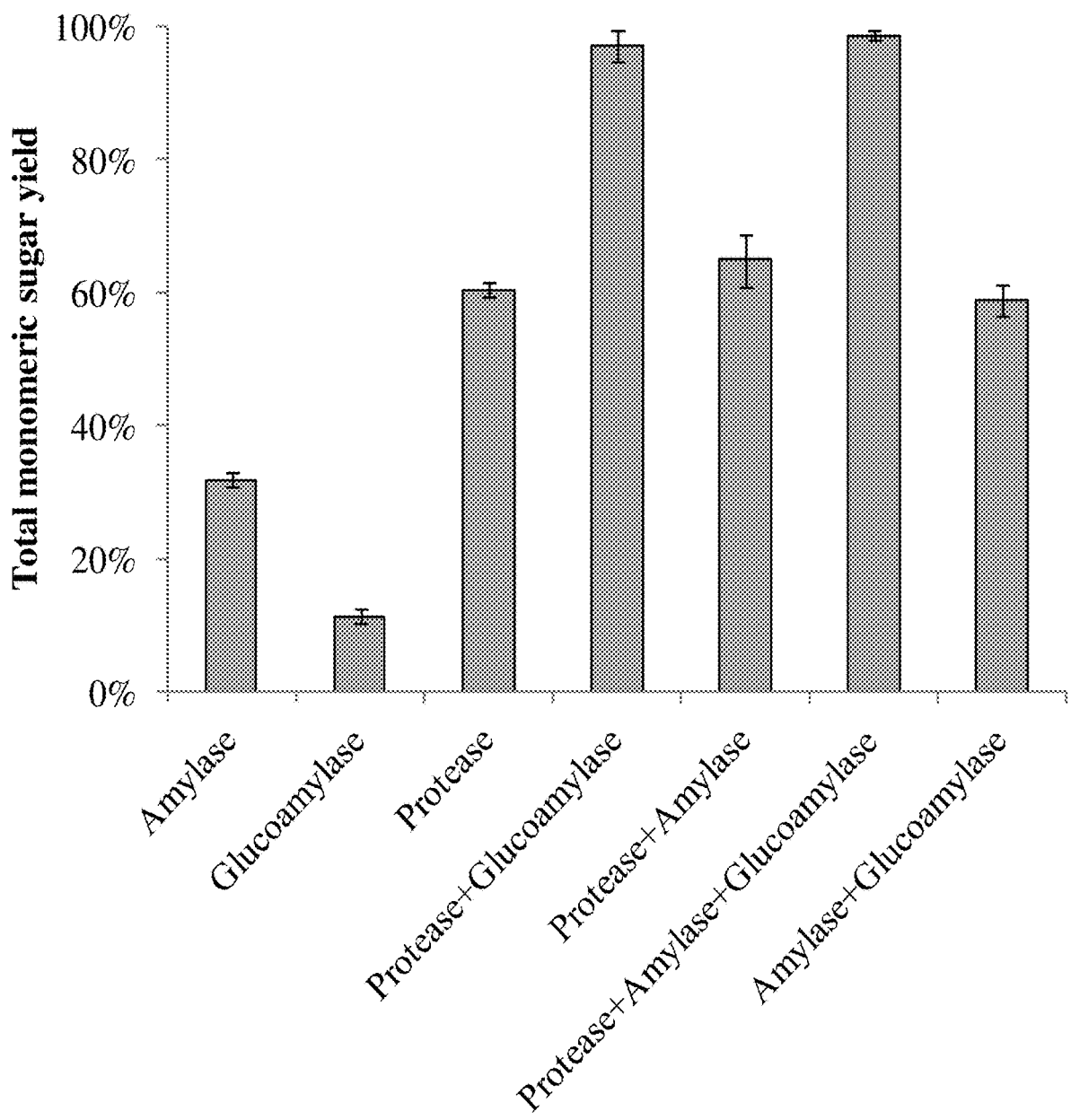
FIG. 11: Effect of the enzyme cocktail composition on sugar release. Experiments were performed using a 16% (w/v) microalgae biomass solution for 2 h with different combinations of α-amylase, glucoamylase, and protease. The y-axis shows release of monomeric sugars relative to the total carbohydrate initially present in the biomass.
Figure 12:
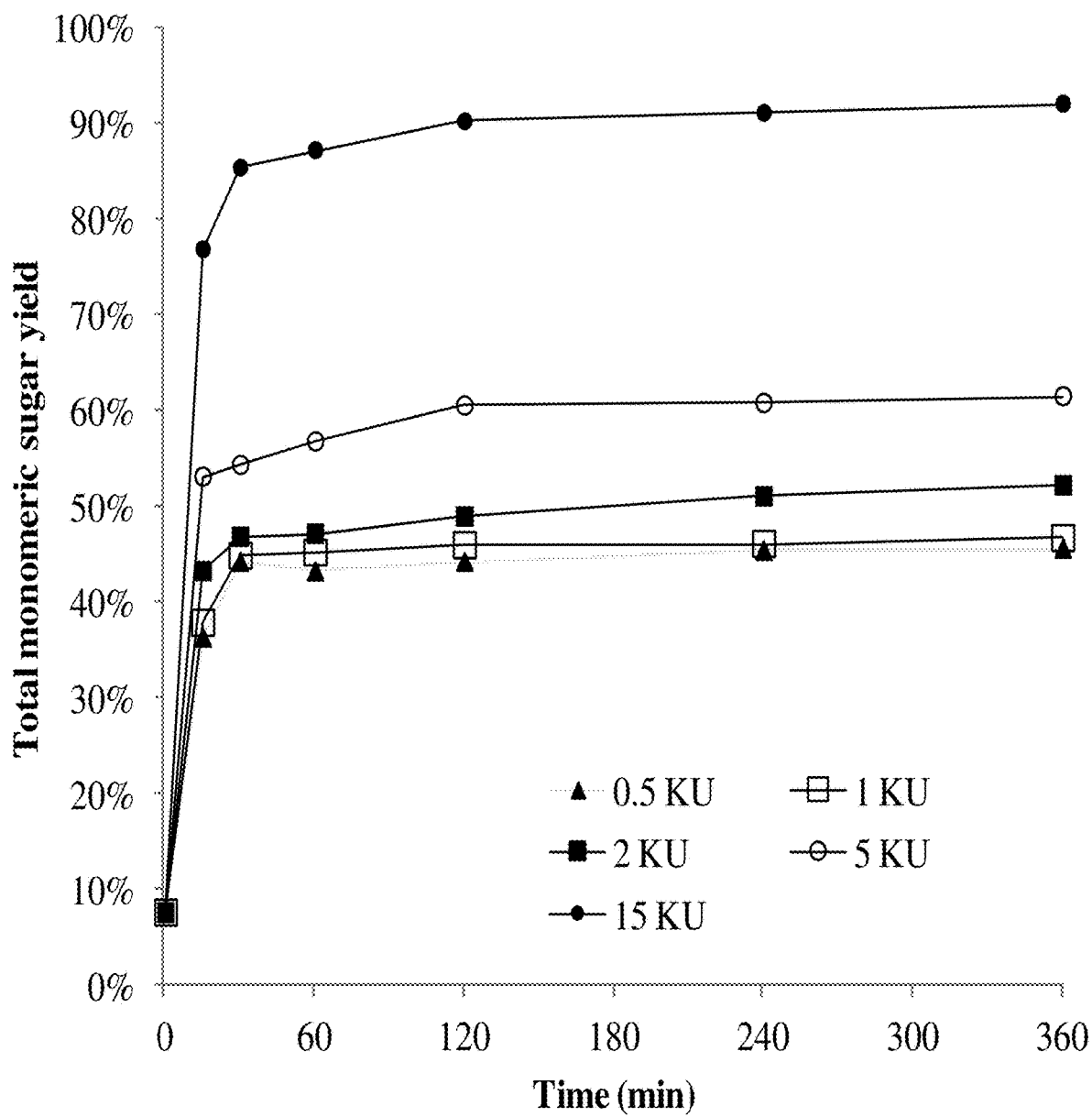
FIG. 12: Sugar release during digestion of algal biomass with varying loadings of α-amylase (0.5-15 kU) and fixed glucoamylase loadings (150 U). Experiments were performed using a 16% (w/v) microalgae biomass solution at a pH of 4.5 and 55° C. The y-axis shows release of monomeric sugars relative to the total carbohydrate initially present in the biomass.

The results (FIG. 11) show that treatments with protease alone resulted in the release of a significant amount of monomeric sugars. Without wishing to be bound by theory, it is believed this is possibly due to presence of small amounts of α-amylase and glucoamylase in this enzyme preparation, as previously discussed in Example 1 (FIG. 10). Supplementation of protease with additional α-amylase did not increase sugar yield, indicating that α-amylase activity was not limiting in this system. However, addition of glucoamylase to protease or to a mixture of protease and α-amylase resulted in near complete breakdown of the available polysaccharides to monomeric sugars, indicating that insufficient glucoamylase activity was available in both the commercial protease and α-amylase preparations. Digestion experiments performed with a mixture of α-amylase and glucoamylase showed better yields than digestions performed with the individual enzymes. However, lesser yields were observed than in treatments that contained protease, indicating that either protease activity was necessary for accessing intracellular carbohydrates or that the α-amylase concentrations used in these experiments were insufficient to break down all available polysaccharides.

Figure 13:
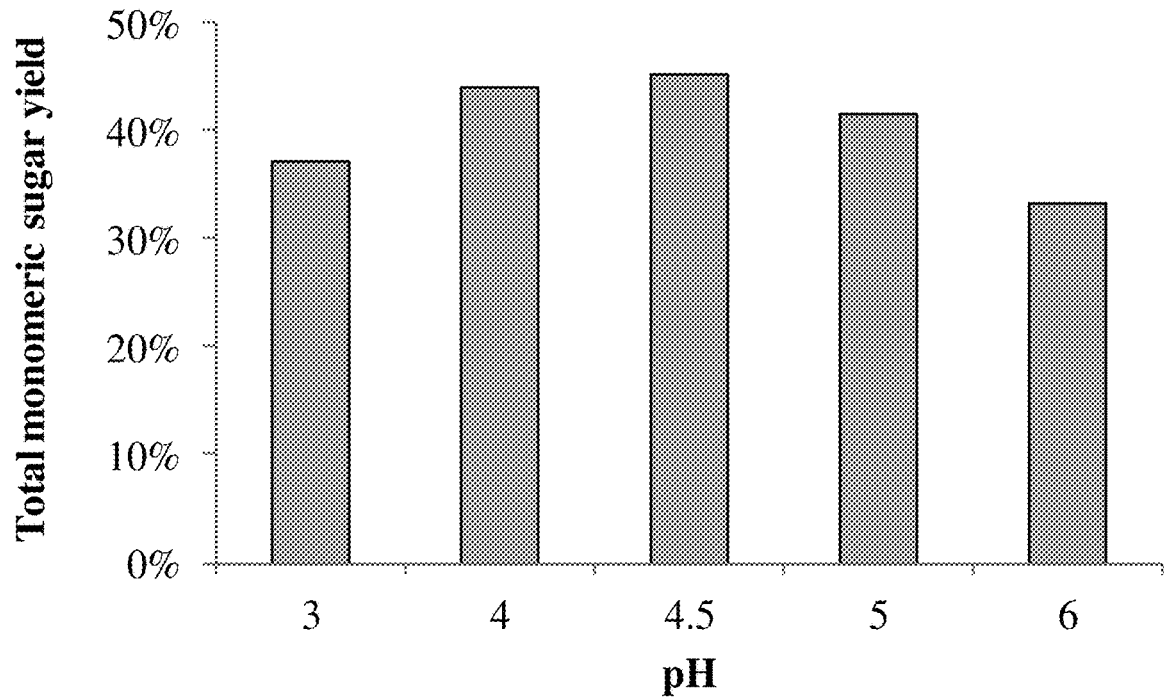
FIG. 13: Sugar release as a function of pH during digestion of algal biomass with α-amylase (1 kU) and glucoamylase loadings (150 U). Experiments were performed using a 16% (w/v) microalgae biomass solution at 55° C. The y-axis shows release of monomeric sugars relative to the total carbohydrate initially present in the biomass.

To determine if additional α-amylase (in combination with glucoamylase) results in higher recovery of monomeric sugars, experiments were performed at α-amylase loadings between 0.5 and 15 kU. 150 U of glucoamylase was also added to the solution. Results of these experiments (FIG. 13) show that at α-amylase loading below 5 kU, less than 60% of the biomass carbohydrates were converted to monomeric sugars. However, at an α-amylase loading of 15 kU, nearly 90% of the polysaccharides were hydrolyzed to sugars. These results show that by appropriately adjusting levels of α-amylase and glucoamylase, nearly complete hydrolysis of algal polysaccharides is possible. To determine optimum pH of this enzyme combination, experiments were performed using a mixture of 1 kU α-amylase and 150 U glucoamylase at media pH values between 3 and 6. Results of these experiments (FIG. 13) show that the highest activity is obtained between pH of 4 and 5.

Figure 14:
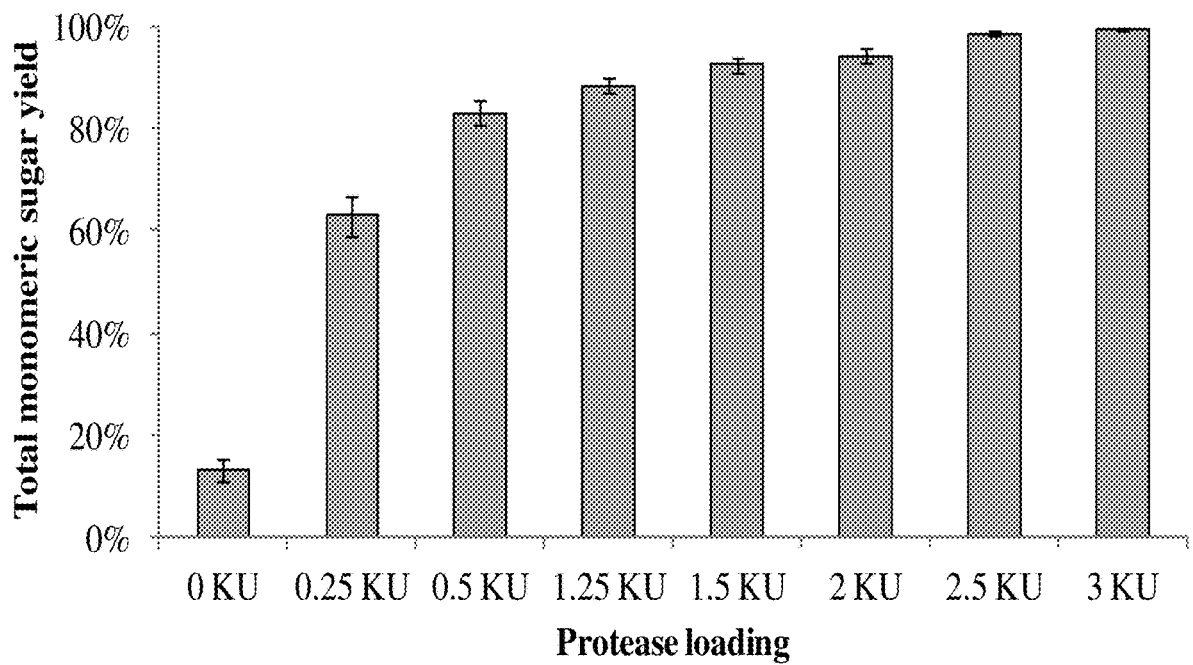
FIG. 14: Sugar release during digestion of algal biomass with varying loadings of protease (0-3 kU) and fixed glucoamylase loadings (150 U). Experiments were performed using a 16% (w/v) microalgae biomass solution at a pH of 4.5 and 55° C. The y-axis shows release of monomeric sugars relative to the total carbohydrate initially present in the biomass.

As discussed above, from the results presented in FIG. 11, algal carbohydrate hydrolysis can also be accomplished using mixtures of protease and glucoamylase. To determine the effect of protease on sugar recovery, experiments were performed at protease loadings varying from 0 to 3 kU and with a fixed glucoamylase loading of 150 U. The results show that greater than 90% of the algal carbohydrates can be converted into monomeric sugars at protease loadings of more than 1.25 kU (FIG. 14).

Figure 15:
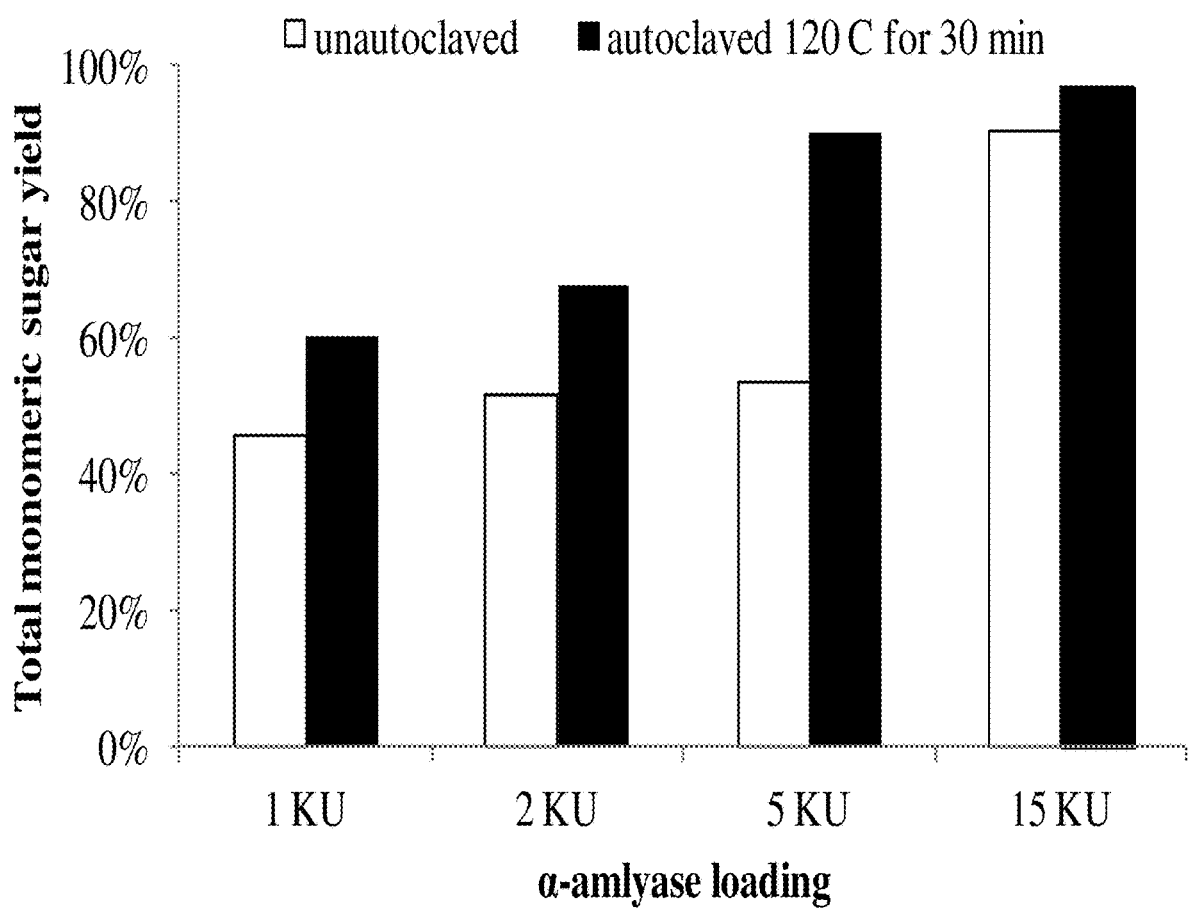
FIG. 15: Sugar release during digestion of algal biomass with varying loadings of protease (0-3 kU) and fixed glucoamylase loadings (150 U). Experiments were performed using a 16% (w/v) microalgae biomass solution at a pH of 4.5 and 55° C. The y-axis shows release of monomeric sugars relative to the total carbohydrate initially present in the biomass.

Example 3: Sugar Recovery from Microalgal Biomass by Hydrothermal Pretreatment Followed by Enzymatic Digestion Hydrothermal pretreatment was used in combination with enzymatic digestion to evaluate the potential for lowering enzyme requirements for sugar recovery. For the hydrothermal treatment, algal slurries (16% w/w) were loaded into sealed serum bottles and autoclaved at 120° C. for 30 minutes. After cooling to room temperature, the pretreated slurries were digested at 55° C. for 6 h using a mixture of α-amylase and glucoamylase (pH=4.5). A series of digestions were performed with α-amylase loadings between 0.5 and 15 kU while maintaining a glucoamylase loading of 150 U. Monomeric sugar release was measured at the end of the experiments. As seen from FIG. 15, the pretreatment improved enzymatic digestibility relative to controls which were not thermally pretreated. As a result, up to 90% sugar recovery was able to be achieved at α-amylase loadings as low as 5 kU.

Example 4: Fermentation of Digested Microalgal Biomass to Succinic Acid

Succinic acid fermentation experiments were conducted for enzymatically hydrolyzed algae biomass under 4 conditions with 3 model sugar solutions as controls. First, 16% (w/v) algal biomass slurries were digested at 50° C. for 2 h using a mixture of protease and glucoamylase as described in Example 2. A portion of the digested slurry was centrifuged (5000 rpm, 10 min) to separate out the solids. Fermentations were performed with the whole digestate as well as with the supernatant both with and without yeast extract (2 g/L) as additional nutrient source. As controls, model sugar solutions with the same sugar concentration as the digestate along with 2 g/L, 5 g/L, or 10 g/L of yeast extract were also fermented.

*Actinobacillus succinogenes* type strain 130Z (ATCC 55618) was used as the fermenting organism. The strain was cultured in tryptic soy broth and a second-generation liquid culture was used as inoculum. $MgCO_3$ (~40 g/L) was added to the fermentation media as a pH buffer. A 4% (v/v) inoculum was used and fermentations were performed at 37° C. in 50 mL serum bottles that contained sterile carbon dioxide. Soluble nitrogen was analyzed using a cadmium reduction method, which converted the nitrate to nitrite, as determined by spectrophotometer. Sugars and organic acids in the samples were analyzed via HPLC.

Figure 16A:
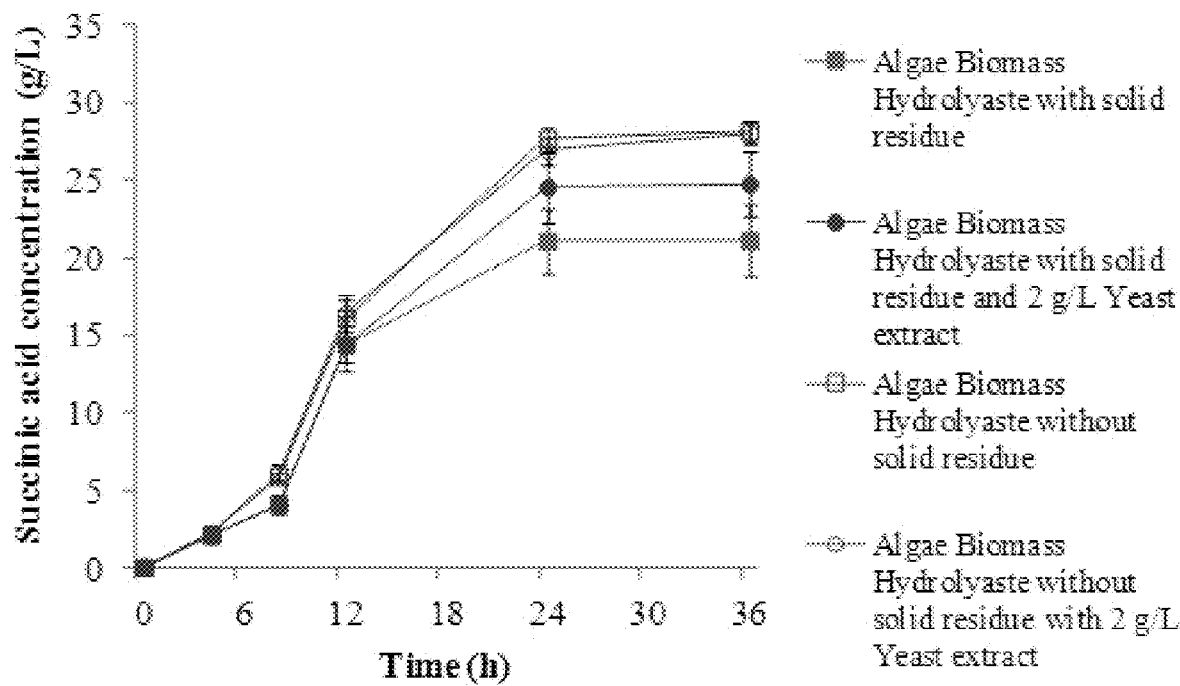
FIGS. 16A-16B: Fermentation of digested microalgal biomass (FIG. 16A) and glucose to succinic acid (FIG. 16B).
Figure 16B:
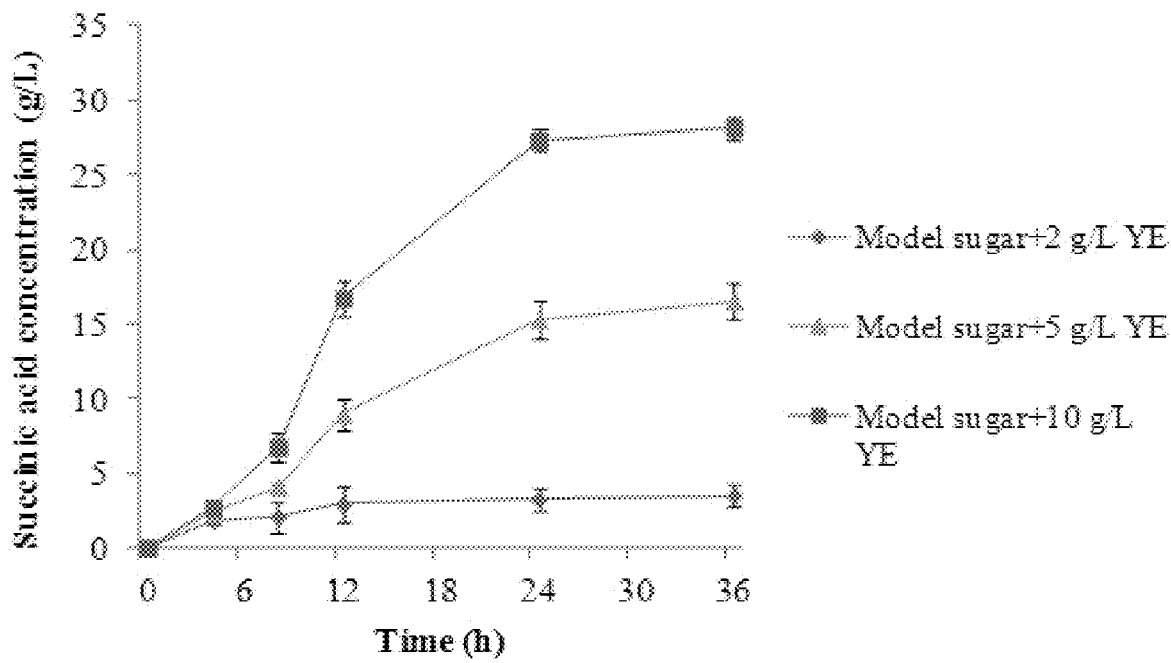

External supplementation of the hydrolysate with yeast extract showed no significant difference on the succinic acid fermentation (FIGS. 16A-16B). The succinic acid production from the microalgae hydrolysate was similar to the model sugar control fermentation containing 10 g/L yeast extract as the nitrogen source. Thus, the nitrogen and micronutrients available in the hydrolysate itself were comparable to those provided by the yeast extract. Hence, for succinic acid fermentation of the algae biomass hydrolysate, no external nitrogen source or other nutrient is required.

TABLE 1

Nitrogen content change in the fermentation

| | After enzymatic hydrolysis | After 24 hours fermentation with algae residue | After 24 hours fermentation without algae residue |
|---|---|---|---|
| Soluble nitrogen content | 27.89 mg/L | 21.29 mg/L | 17.30 mg/L |

As shown in Table 1, the soluble nitrogen content remaining after the fermentation of the microalgae hydrolysate with the solid residue was higher than the clarified hydrolysate. This indicates that soluble nitrogen is released from the solid residue during the fermentation.

Certain embodiments of the methods and products disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A method of enzymatic hydrolysis for converting algal carbohydrates into monomeric sugars, comprising:
    digesting microalgae with a mixture of enzymes in a single step to produce an enzymatically treated biomass, wherein the enzyme mixture comprises at least one acid protease at an acid protease loading of at least 0.25 kU protease per gram of biomass and at least one glucoamylase;
    thereafter, separating the enzymatically treated biomass into a solid phase and an aqueous phase, wherein the aqueous phase comprises at least monomeric sugars,
    wherein conversion of monomeric sugars from algal carbohydrates is at least 60%, and
    wherein the microalgae is digested at a pH of from 3.0 to 5.5.

2. The method of claim 1, comprising further processing and/or separating one or both of the solid phase and the aqueous phase to obtain lipids, proteins, or solids, or bio-based products.

3. The method of claim 2, wherein the further processing and/or separating comprises subjecting an organic phase to a lipid-solvent separation to recover lipids.

4. The method of claim 2, wherein the further processing comprises:
    subjecting the aqueous phase to microbial fermentation to obtain a bio-based product.

5. The method of claim 4, wherein the bio-based product comprises succinic acid.

6. The method of claim 1, further comprising extracting lipids from the solid phase with an organic solvent.

7. The method of claim 1, wherein the microalgae is lipid-rich wet microalgae.

8. The method of claim 1, wherein at least one of the enzymes is of fungal origin.

9. The method of claim 1, wherein the mixture comprises the glucoamylase in an amount of at least 150 U glucoamylase per gram of biomass.

10. The method of claim 1, wherein the mixture further comprises at least one α-amylase.

11. The method of claim 1, wherein the enzymatically treated microalgae has a lipid content below 5% w/w.

12. The method of claim 1, wherein the separating comprises filtering the enzymatically treated biomass.

13. The method of claim 2, wherein the further processing and/or separating comprises filtering the aqueous phase.

14. A method of obtaining monomeric sugars from microalgae, comprising: digesting microalgae with a mixture of enzymes in one step to produce a digested biomass, wherein the enzyme mixture comprises at least one acid protease at an acid protease loading of at least 0.25 kU protease per gram of biomass and at least one glucoamylase; and thereafter, separating the digested biomass into a solid phase and an aqueous phase using a filtration step, wherein the solid phase contains lipids and the aqueous phase contains carbohydrates and monomeric sugars; wherein conversion of algal carbohydrates into monomeric sugars is at least 60%; and wherein the microalgae is digested at a pH of from 3.0 to 5.5.

* * * * *